United States Patent
Kimura et al.

(10) Patent No.: US 10,631,773 B2
(45) Date of Patent: Apr. 28, 2020

(54) LIVING BODY STATE ESTIMATION APPARATUS, LIVING BODY STATE ESTIMATING METHOD, AND NON-TRANSITORY COMPUTER-READABLE MEDIUM

(71) Applicant: TOHOKU UNIVERSITY, Sendai-shi, Miyagi (JP)

(72) Inventors: Yoshitaka Kimura, Sendai (JP); Nobuo Yaegashi, Sendai (JP); Kunihiro Okamura, Sendai (JP); Takuya Ito, Sendai (JP); Kunihiro Koide, Sendai (JP); Miyuki Endo, Sendai (JP)

(73) Assignee: TOHOKU UNIVERSITY, Sendai-shi Miyagi (JP)

( * ) Notice: Subject to any disclaimer, the term of this patent is extended or adjusted under 35 U.S.C. 154(b) by 0 days.

(21) Appl. No.: 15/273,976

(22) Filed: Sep. 23, 2016

(65) Prior Publication Data
US 2017/0027497 A1    Feb. 2, 2017

Related U.S. Application Data

(63) Continuation of application No. PCT/JP2014/058589, filed on Mar. 26, 2014.

(51) Int. Cl.
*A61B 5/04* (2006.01)
*A61B 5/00* (2006.01)
(Continued)

(52) U.S. Cl.
CPC .......... *A61B 5/4362* (2013.01); *A61B 5/0245* (2013.01); *A61B 5/02411* (2013.01);
(Continued)

(58) Field of Classification Search
CPC . A61B 5/4362; A61B 5/4312; A61B 5/02411; A61B 5/0245; A61B 5/0444;
(Continued)

(56) References Cited

U.S. PATENT DOCUMENTS

| | | | |
|---|---|---|---|
| 5,957,855 A * | 9/1999 | Oriol | A61B 5/02411 600/408 |
| 7,333,850 B2 * | 2/2008 | Marossero | A61B 5/02411 600/511 |

(Continued)

FOREIGN PATENT DOCUMENTS

| JP | 59-120135 A | 7/1984 |
|---|---|---|
| JP | 2006-204759 A | 8/2006 |

OTHER PUBLICATIONS

Jafari, Maria, et al. "Fetal Electrocardiogram Extraction by Sequential Separation in the Wavelet Domain". Mar. 3, 2005. IEEE Transactions on Biomedical Engineering. vol. 52, No. 3.*

(Continued)

*Primary Examiner* — Amanda K Hulbert
(74) *Attorney, Agent, or Firm* — Myers Wolin, LLC

(57) ABSTRACT

A living body state estimation apparatus acquires information indicating a state of a living body. The living body state estimation apparatus is configured to include an electrocardiogram signal acquisition unit which acquires an electrocardiogram signal of the living body and an information acquisition unit which acquires a parameter as the information, the parameter specifying a predetermined function indicating a probability distribution for a reference wave interval which is a time interval between peaks of consecutive predetermined reference waves in the acquired electrocardiogram signal.

18 Claims, 13 Drawing Sheets

(51) Int. Cl.
*A61B 5/0444* (2006.01)
*A61B 5/0456* (2006.01)
*A61B 5/11* (2006.01)
*A61B 5/024* (2006.01)
*A61B 5/0245* (2006.01)
*A61B 5/0472* (2006.01)

(52) U.S. Cl.
CPC .......... *A61B 5/0444* (2013.01); *A61B 5/0456* (2013.01); *A61B 5/1118* (2013.01); *A61B 5/04012* (2013.01); *A61B 5/0472* (2013.01)

(58) Field of Classification Search
CPC . A61B 5/0456; A61B 5/1118; A61B 5/04012; A61B 5/0472
USPC .......................................... 600/511, 516, 517
See application file for complete search history.

(56) References Cited

U.S. PATENT DOCUMENTS

| | | |
|---|---|---|
| 8,175,692 B2 | 5/2012 | Kimura et al. |
| 2002/0052557 A1 | 5/2002 | Griffin et al. |
| 2005/0267376 A1* | 12/2005 | Marossero ......... A61B 5/02411 600/511 |
| 2006/0074329 A1* | 4/2006 | Ferguson, II ...... A61B 5/02411 600/511 |
| 2008/0146953 A1 | 6/2008 | Kimura et al. |
| 2010/0185108 A1 | 7/2010 | Vullings et al. |
| 2011/0092837 A1 | 4/2011 | Lee et al. |
| 2017/0027497 A1* | 2/2017 | Kimura ................ A61B 5/0456 |

OTHER PUBLICATIONS

Sameni et al., "Multichannel ECG and noise modeling: Application to maternal and fetal ECG signals" EURASIP Journal on Advances in Signal Processing, 2007, Article ID 43407.

International Search Report issued for corresponding International Patent Application No. PCT/JP2014/058589, dated Jun. 17, 2014.

Notification of Reasons for Refusal issued by the Japan Patent Office for corresponding Japanese Patent Application No. 2016-509717, dated Oct. 17, 2017, with an English translation.

* cited by examiner

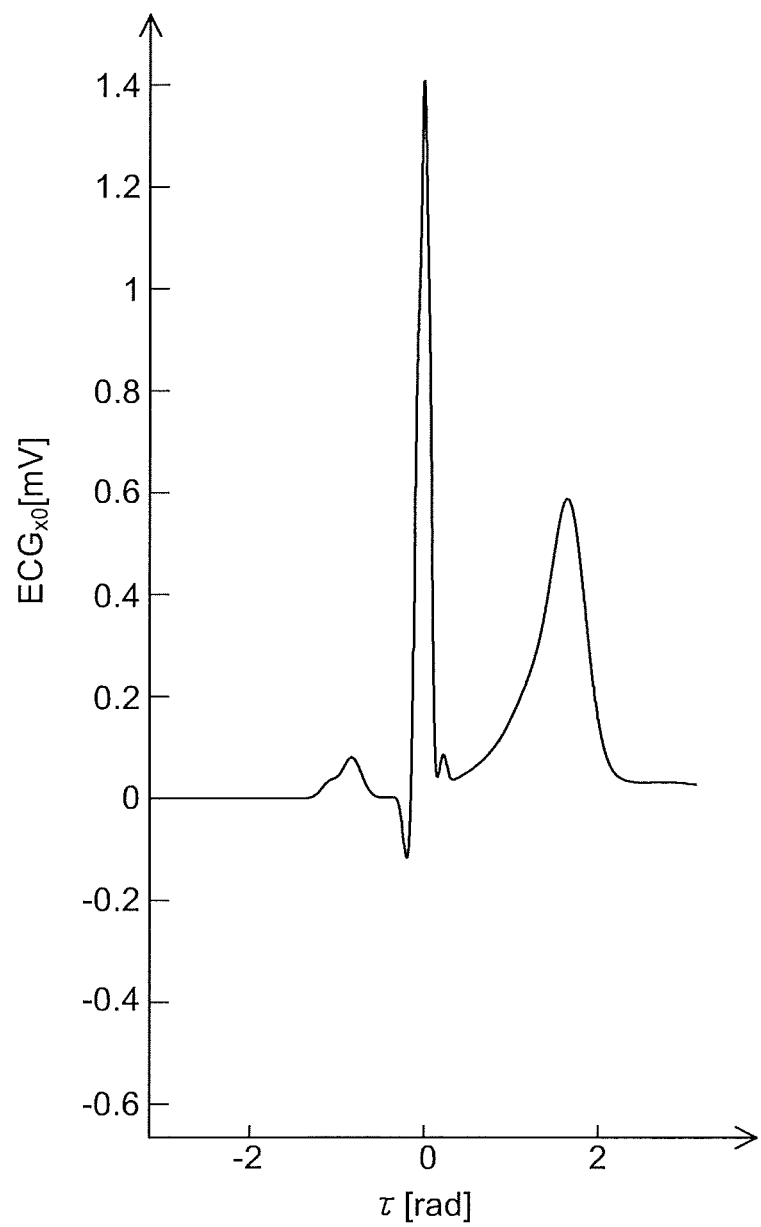

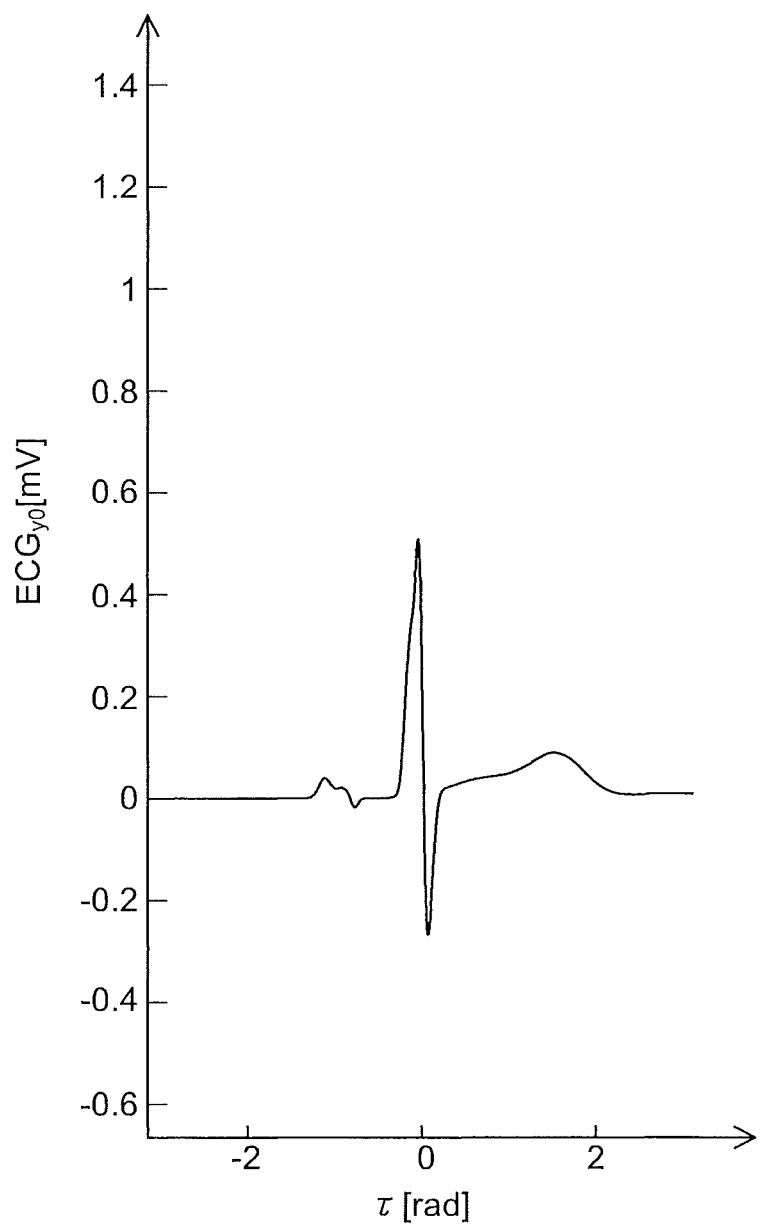

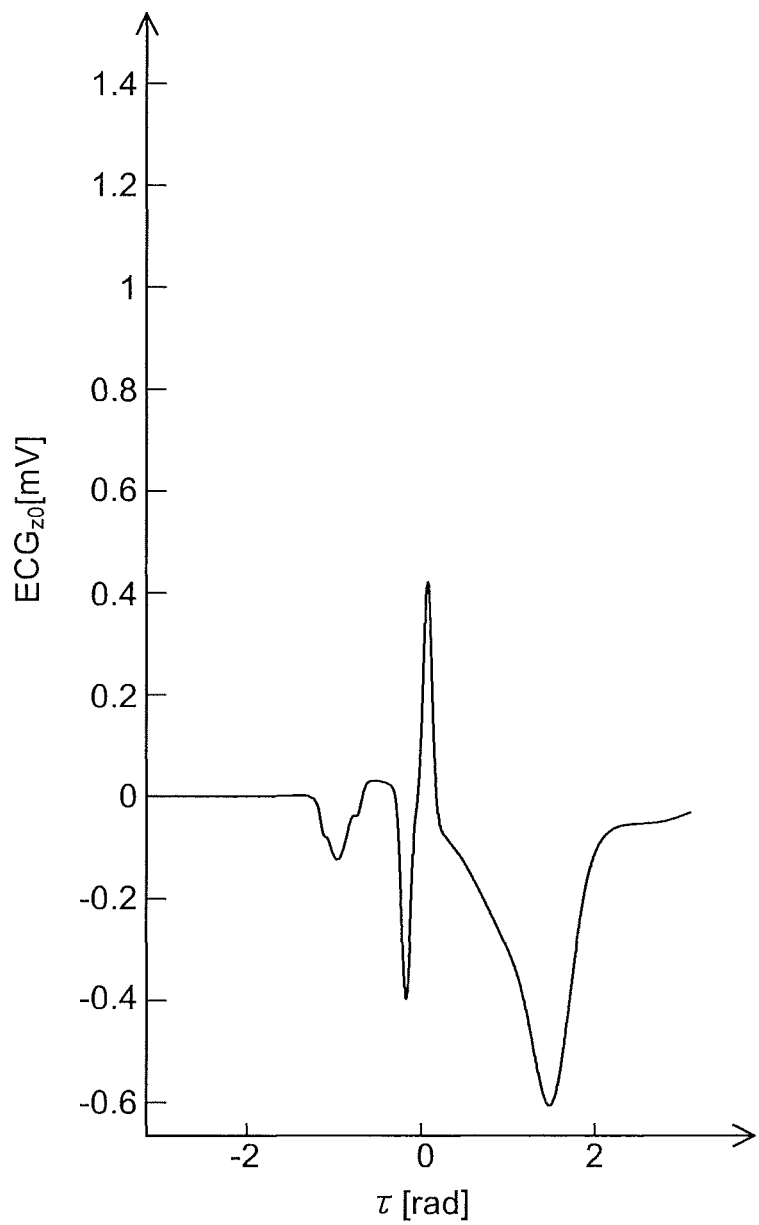

LIVING BODY STATE ESTIMATION APPARATUS, LIVING BODY STATE ESTIMATING METHOD, AND NON-TRANSITORY COMPUTER-READABLE MEDIUM

CROSS-REFERENCE TO RELATED APPLICATION

The present application is a continuation application of International Application No. PCT/JP2014/058589, filed on Mar. 26, 2014, now expired. The International Publication No. of the above-identified International Application is WO 2015/145625 A1. The contents of this application are incorporated herein by reference in their entirety.

FIELD

The present invention relates to a living body state estimation apparatus, a living body state estimating method, and a living body state estimating program.

BACKGROUND

An electrocardiogram signal indicating a change in electromotive force of heart is estimated by measuring a potential signal indicating a change in potential on a surface of a living body through electrodes attached to the surface of the living body. As illustrated in FIG. 1, the electrocardiogram signal includes waves having peaks called a P wave WP, a Q wave WQ, an R wave WR, an S wave WS, and a T wave WT at every beating. Time intervals between peaks of each wave in the electrocardiogram signal are used for diagnosis, test, or the like of disease. The heart rate is measured, for example, by acquiring the time interval between the peaks of consecutive R waves WR.

There are known living body state estimation apparatuses which acquire information indicating a state of a living body. As one of this type of living body state estimation apparatuses, a living body state estimation apparatus disclosed in Patent Literature 1 acquires an RR interval which is a time interval between peaks of consecutive R waves based on an electrocardiogram signal of the living body. The living body state estimation apparatus calculates an average value of the acquired RR intervals.

The living body state estimation apparatus calculates a first parameter based on a deviation from the average value for each of the RR intervals which are smaller than the average value among the acquired RR intervals. The living body state estimation apparatus calculates a second parameter based on a deviation from the average value for each of the RR intervals which are larger than the average value among the acquired RR intervals. Next, the living body state estimation apparatus acquires a ratio of the first parameter and the second parameter as information indicating asymmetry of RR intervals.

Patent Literature 1: US 2002/052557 A.

SUMMARY

However, there are some cases where the ratios of the first parameter and the second parameter are equal in two states where probability distributions of RR intervals are relatively greatly different from each other. In other words, there are some cases where the ratio of the first parameter and the second parameter cannot represent the probability distribution of an RR interval with sufficiently high accuracy.

Therefore, in the living body state estimation apparatus, there is a problem in that it is not possible to acquire information indicating a state of a living body with high accuracy.

The present invention is to solve the above-described problem in that it is not possible to acquire information indicating a state of a living body with high accuracy.

According to an aspect of the present invention, there is provided a living body state estimation apparatus which acquires information indicating a state of a living body.

Furthermore, the living body state estimation apparatus includes an electrocardiogram signal acquisition unit which acquires an electrocardiogram signal of the living body and an information acquisition unit which acquires a parameter as the information, the parameter specifying a predetermined function indicating a probability distribution for a reference wave interval which is a time interval between peaks of consecutive predetermined reference waves in the acquired electrocardiogram signal.

According to another aspect of the present invention, there is provided a living body state estimating method which acquires information indicating a state of a living body.

Furthermore, the living body state estimating method includes acquiring an electrocardiogram signal of the living body and acquiring a parameter as the information, the parameter specifying a predetermined function indicating a probability distribution for a reference wave interval which is a time interval between peaks of consecutive predetermined reference waves in the acquired electrocardiogram signal.

According to still another aspect of the present invention, there is provided a living body state estimating program for causing a computer to execute a process of acquiring information indicating a state of a living body.

Furthermore, the living body state estimating program causes a computer to execute a process including acquiring an electrocardiogram signal of the living body and acquiring a parameter as the information, the parameter specifying a predetermined function indicating a probability distribution for a reference wave interval which is a time interval between peaks of consecutive predetermined reference waves in the acquired electrocardiogram signal.

According to a living body state estimation apparatus disclosed, it is possible to acquire information indicating a state of a living body with high accuracy.

BRIEF DESCRIPTION OF DRAWINGS

FIG. 6 is a graph illustrating an example of a reference fetal electrocardiogram signal used by the fetal state estimation apparatus illustrated in FIG. 2.

FIG. 7 is a graph illustrating an example of a reference fetal electrocardiogram signal used by the fetal state estimation apparatus illustrated in FIG. 2.

FIG. 8 is a graph illustrating an example of a reference fetal electrocardiogram signal used by the fetal state estimation apparatus illustrated in FIG. 2.

DESCRIPTION OF EMBODIMENTS

Hereinafter, embodiments of a living body state estimation apparatus, a living body state estimating method, and a living body state estimating program according to the present invention will be described with reference to FIGS. 2 to 16.

First Embodiment (Configuration)

Figure 1:
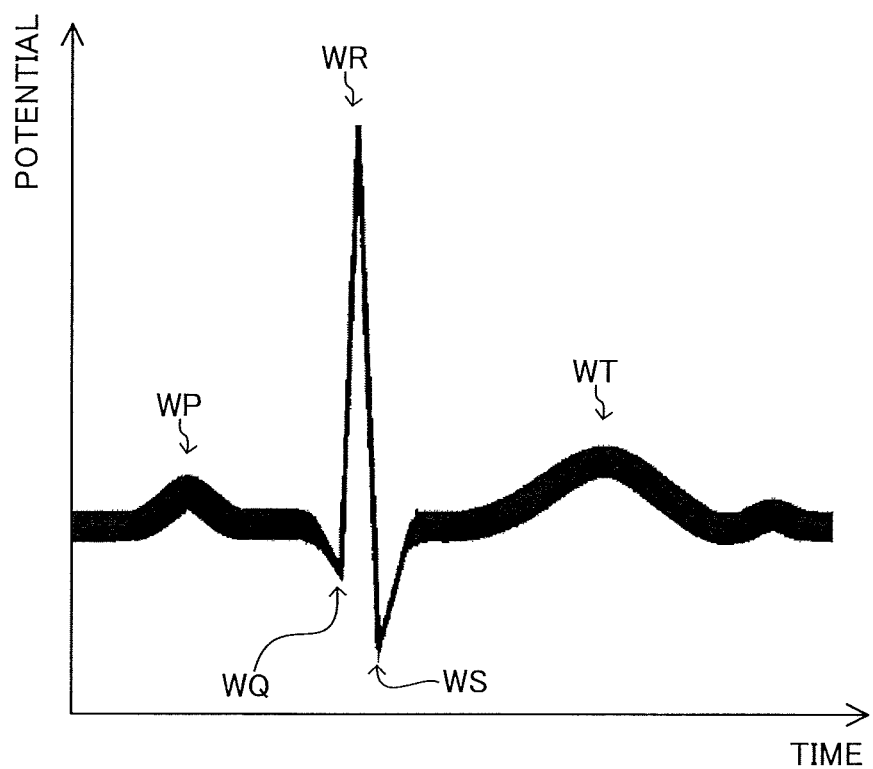
FIG. 1 is a diagram illustrating an example of an electrocardiogram signal.
Figure 2:
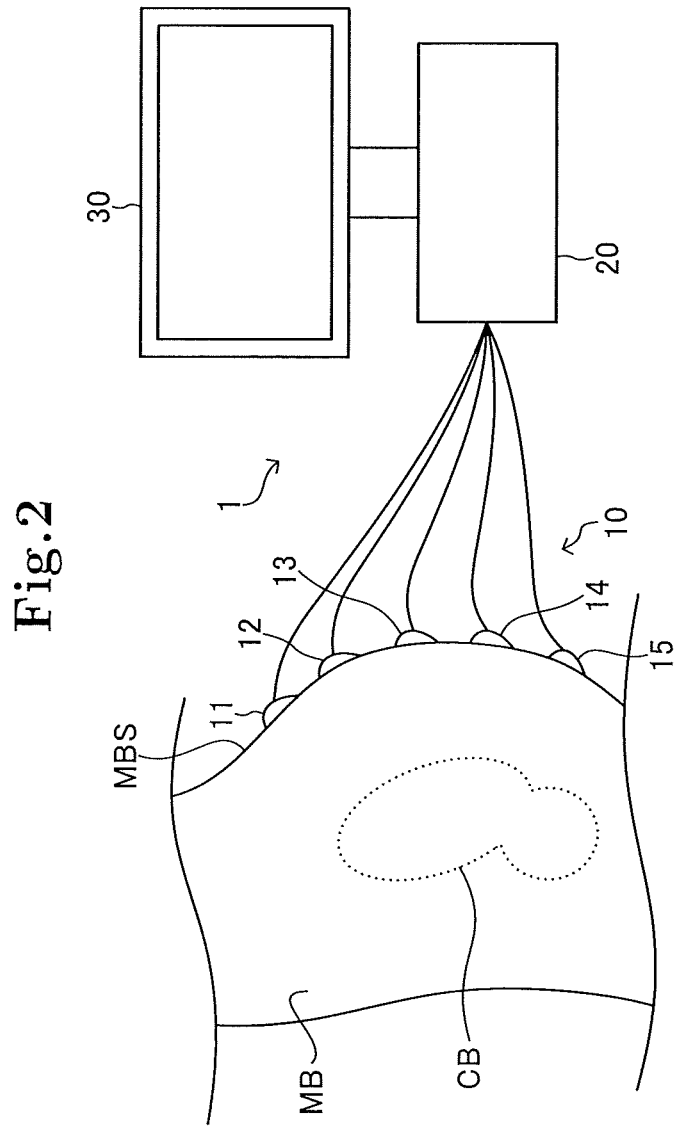
FIG. 2 is a diagram illustrating an example of a configuration of a fetal state estimation apparatus according to a first embodiment.

As illustrated in FIG. 2, a fetal state estimation apparatus 1 according to a first embodiment is configured to include a measurement unit 10, a processing unit 20, and an output unit 30. The fetal state estimation apparatus 1 is an example of the living body state estimation apparatus.

The measurement unit 10 is configured to include electrodes 11 to 15. Although FIG. 2 illustrates an example where the measurement unit 10 includes five electrodes, the number of electrodes included in the measurement unit 10 may be four or less and six or more. The electrodes 11 to 15 are attached on a surface MBS (for example, skin) of the abdomen of a pregnant material body MB.

The measurement unit 10 measures a bio-potential signal indicating a change in potential on the surface MBS of the material body MB through the electrodes 11 to 15.

The bio-potential signal is a superposition of a maternal body electrocardiogram base signal caused by the beating of the heart of the material body MB, a maternal body electromyogram base signal caused by activity of muscle fibers of the material body MB, a fetal electrocardiogram base signal caused by the beating of the heart of the fetus CB accommodated in the uterus of the material body MB, noises, and the like.

Figure 3:
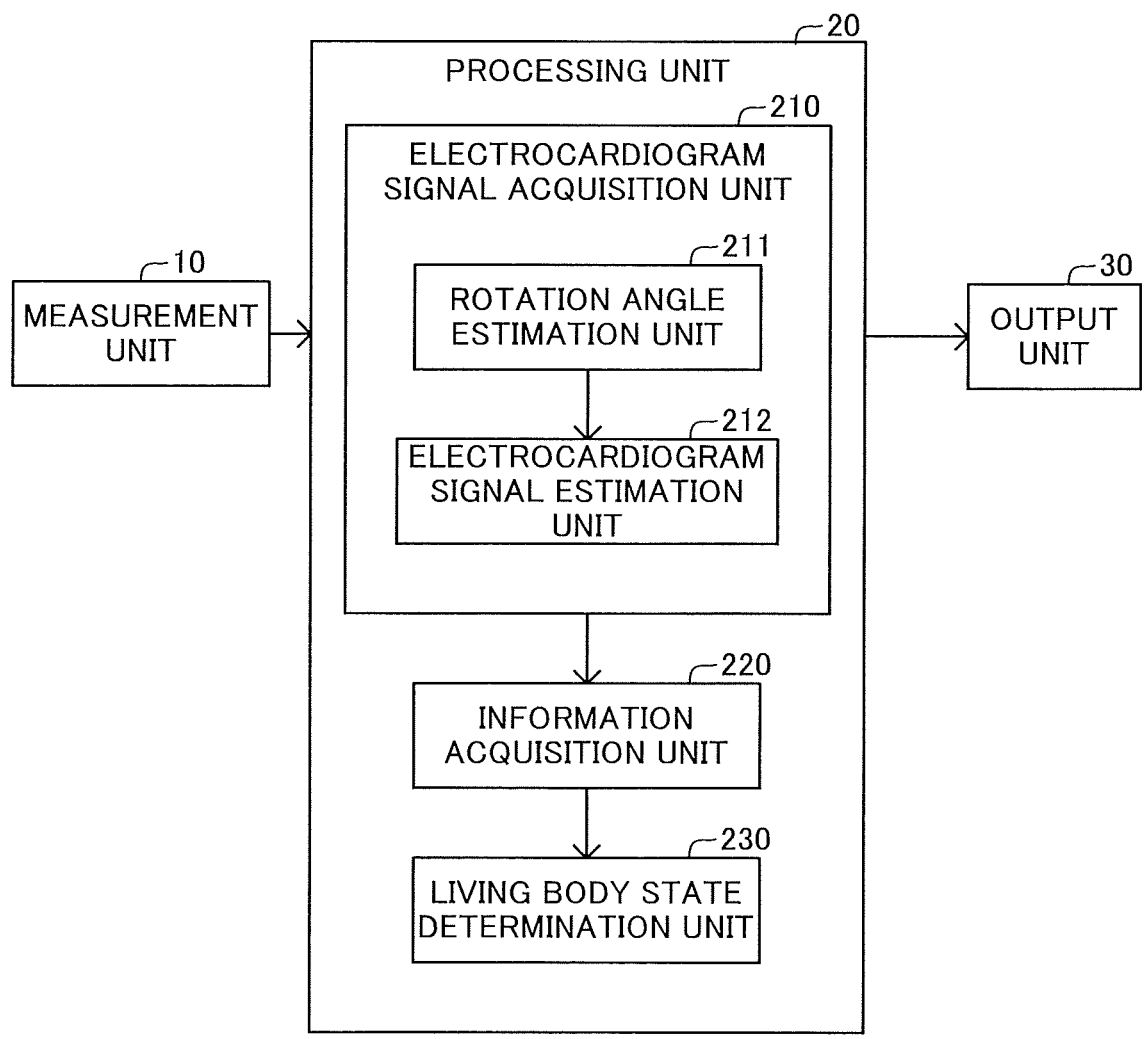
FIG. 3 is a block diagram illustrating an example of functions of a processing unit illustrated in FIG. 2.

The processing unit 20 processes the bio-potential signal measured by the measurement unit 10. As illustrated in FIG. 3, functions of the processing unit 20 include an electrocardiogram signal acquisition unit 210, an information acquisition unit 220, and a living body state determination unit 230.

In the example, the processing unit 20 is configured to include a processing device (for example, a CPU (Central Processing Unit), a DSP (Digital Signal Processor), or the like) and a storage device, and implements the functions by causing the processing device to execute a fetal state estimating program stored in the storage device in advance. The processing unit 20 may implement at least a portion of the functions using an integrated circuit (for example, LSI (Large Scale Integration) or the like).

The electrocardiogram signal acquisition unit 210 acquires an electrocardiogram signal of the fetus CB in the maternal body MB based on the bio-potential signal measured by the measurement unit 10. In the example, the electrocardiogram signal acquisition unit 210 is configured to include a rotation angle estimation unit 211 and an electrocardiogram signal estimation unit 212.

The rotation angle estimation unit 211 extracts a fetal electrocardiogram base signal from a bio-potential signal measured by the measurement unit 10 using an Independent Component Analysis (ICA).

For example, the ICA is a natural gradient method, a Fast ICA method, or a reference-based ICA method. As disclosed in Patent Literature 2 (JP 2006-204759 A), the reference-based ICA method is a method of generating a reference signal based on a beating period signal indicating a period of beating of the heart of the fetus and extracting a fetal electrocardiogram base signal from a bio-potential signal based on the generated reference signal. Herein, the beating period signal may also be generated based on the bio-potential signal. The beating period signal may also be a signal measured by an ultrasonic sensor.

The rotation angle estimation unit 211 may also extract the fetal electrocardiogram base signal after performing a reduction process of reducing the maternal body electrocardiogram base signal from the measured bio-potential signal. In this case, for example, the rotation angle estimation unit 211 may estimate the maternal body electrocardiogram base signal through the electrodes (not shown) attached to the chest of the maternal body MB, and may perform the reduction process based on the estimated maternal body electrocardiogram base signal.

The rotation angle estimation unit 211 may extract the fetal electrocardiogram base signal after reducing the noise by applying a band pass filter. For example, the rotation angle estimation unit 211 may use a band pass filter having a band from 20 Hz to 30 Hz as a pass band.

Figure 4:
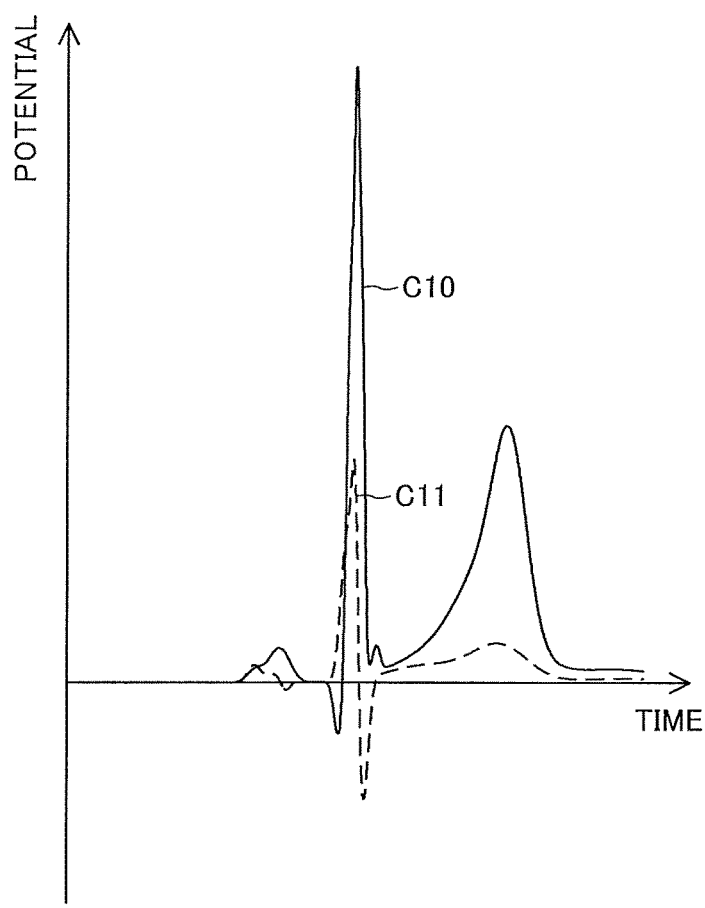
FIG. 4 is a graph illustrating an example of two biopotential signals measured in two states where positions of electrodes with respect to the heart are different from each other.

It is known that, in two states where positions of the electrodes with respect to the heart are different from each other, even in the case where a change in electromotive force of heart is the same, the appearing shapes of the change in electromotive force of heart in the measured bio-potential signals are different from each other. FIG. 4 illustrates two bio-potential signals C10 and C11 measured in the two states where the positions of the electrodes with respect to the heart are different from each other even in the case where the change in electromotive force of heart is the same. For example, as illustrated in FIG. 4, the magnitude and timing of peak of each wave is changed according to the position of the electrode with respect to the heart.

The fetus CB performs rotational movement with respect to the maternal body MB during a relatively short time interval. Therefore, the appearing shape of the change in electromotive force of heart of the fetus CB in the bio-potential signal measured through the electrodes 11 to 15 attached to the surface MBS of the maternal body MB is easily changed according to the rotation of the fetus CB.

The fetal state estimation apparatus 1 according to the first embodiment estimates the rotation angle of the fetus CB with respect to the maternal body MB and acquires the electrocardiogram signal (fetal electrocardiogram signal) of the fetus CB with respect to a predetermined reference rotation angle based on the estimated rotation angle. The appearing shape of the change in electromotive force of heart of the fetus CB in the fetal electrocardiogram signal is constant. Therefore, it is possible to acquire information indicating the state of the fetus CB with high accuracy based on the fetal electrocardiogram signal.

In the example, the rotation angle estimation unit 211 estimates the rotation angle of the fetus CB with respect to the maternal body MB based on the extracted fetal electrocardiogram base signal. Hereinafter, the estimation of the rotation angle will be described.

Figure 5:
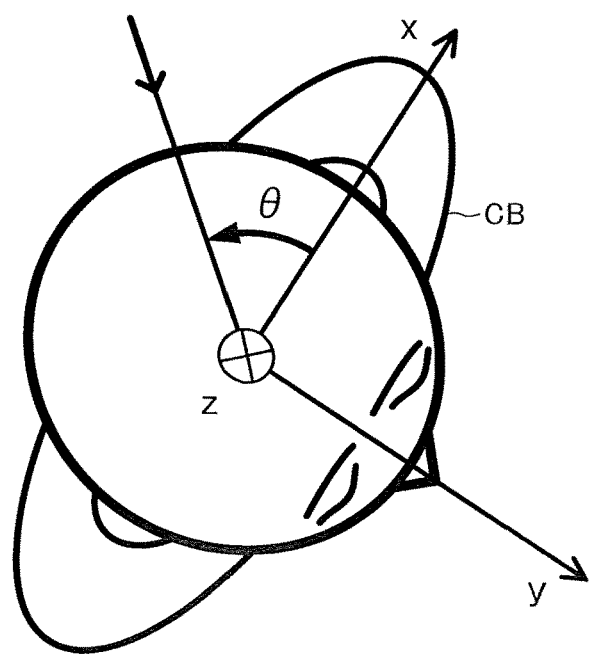
FIG. 5 is a diagram illustrating an example of a coordinate system used by the fetal state estimation apparatus illustrated in FIG. 2.

First, a coordinate system will be described. In the example, as illustrated in FIG. 5, a right-handed rectangular coordinate system is used. In the rectangular coordinate system, the forward direction of the fetus CB is set to the y axis, the downward direction of the fetus CB is set to the z axis, and the leftward direction of the fetus CB is set to the x axis. The rotation angle $\theta$ with respect to the fetus CB is an angle rotated counterclockwise from the x axis as the fetus CB is seen in the positive direction of the z axis.

In the example, the case where the up/down direction of the fetus CB is the up/down direction of the maternal body MB are coincident with each other is assumed. Therefore, in the example, the rotational movement of the fetus CB is movement where the fetus CB rotates about the z axis as the center axis of rotation. The fetal state estimation apparatus 1 may also be applied to the case where the up/down direction of the fetus CB and the up/down direction of the maternal body MB are different from each other.

The fetal electrocardiogram signal $ECG_\theta(\tau)$ of the case where the fetus CB is seen in the direction obtained by rotating the negative direction of the x axis by the rotation angle $\theta$ is expressed by Mathematical Formula 1 based on the fetal electrocardiogram signal $ECG_x(\tau)$ of the case where the fetus CB is seen in the negative direction of the x axis, the fetal electrocardiogram signal $ECG_y(\tau)$ of the case where the fetus CB is seen in the negative direction of the y axis, and the rotation angle $\theta$. $\tau$ denotes a time.

$ECG_\theta(\tau) = \cos(\theta) \cdot ECG_x(\tau) - \sin(\theta) \cdot ECG_y(\tau)$ [Mathematical Formula 1]

Herein, the fetal electrocardiogram signal $ECG_x(\tau)$ may be considered to be a signal indicating an electrocardiogram obtained by projecting a vector electrocardiogram on a left side surface of the fetus CB. The fetal electrocardiogram signal $ECG_y(\tau)$ may be considered to be a signal indicating an electrocardiogram obtained by projecting a vector electrocardiogram on a front surface of the fetus CB.

In the example, by using the ICA to extract the fetal electrocardiogrambase signal, the fetal electrocardiogrambase signal $u_\theta(\tau)$ extracted by the rotation angle estimation unit 211 is normalized so that the average value becomes 0 and the variance becomes 1.

The rotation angle estimation unit 211 estimates the beating time period which is a time period corresponding to the beating based on the extracted fetal electrocardiogram base signal $u_\theta(\tau)$ at every beating of the heart of the fetus CB.

First, the rotation angle estimation unit 211 estimates some time point (for example, a time point in the middle of the time period) in a time period when a state where an absolute value of a value (in the example, potential) of the fetal electrocardiogram base signal $u_\theta(\tau)$ is smaller than a predetermined first threshold value is continuously maintained for longer than a predetermined first threshold value time as the boundary time point.

Next, the rotation angle estimation unit 211 acquires a maximum peak time point $\tau_{max0}$ which is a time point when the fetal electrocardiogram base signal $u_\theta(\tau)$ has a maximum value in a time period between consecutive two boundary time points among the estimated boundary time points.

Then, the rotation angle estimation unit 211 estimates the time period which starts at a time point which is a time of a half of the beating cycle earlier than the maximum peak time point $\tau_{max0}$ and ends at a time point which is a time of a half of the beating cycle later than the maximum peak time point $\tau_{max0}$ as the beating time period. For example, the beating cycle may be acquired by taking autocorrelation to the fetal electrocardiogram base signal $u_\theta(\tau)$.

By doing so, the rotation angle estimation unit 211 estimates the beating time period at every beating of the heart of the fetus CB.

Next, the rotation angle estimation unit 211 estimates the rotation angle $\theta$ for each of the estimated beating time periods.

In the example, the rotation angle estimation unit 211 stores a relationship (first relationship) between the rotation angle and a signal feature amount in advance.

In the example, the signal feature amount is a parameter calculated based on the maximum and minimum values of the fetal electrocardiogram base signal in a QRS wave time period which is a time period corresponding to the QRS wave among the beating time periods. The QRS wave is configured with a Q wave, an R wave, and an S wave.

In the example, the signal feature amount $R(\theta)$ is expressed by Mathematical Formula 2. Herein, $\tau_{max}(\theta)$ denotes a time point (QRS wave time period maximum peak time point) when the fetal electrocardiogram base signal has a maximum value in the QRS wave time period. $\tau_{min}(\theta)$ denotes a time point (QRS wave time period minimum peak time point) when the fetal electrocardiogram base signal has a minimum value in the QRS wave time period. The QRS wave time period is an example of the target time period.

$$R(\theta) = \frac{u_\theta(\tau_{max}(\theta))}{u_\theta(\tau_{max}(\theta)) - u_\theta(\tau_{min}(\theta))}$$ [Mathematical Formula 2]

In the example, the QRS wave time period maximum peak time point $\tau_{max}(\theta)$ is expressed by Mathematical Formula 3, and the QRS wave time period minimum peak time point $\tau_{min}(\theta)$ is expressed by Mathematical Formula 4. Herein, $T_{QRS}$ denotes a length of the QRS wave time period. In the example, $T_{QRS}$ is set to a value obtained by multiplying the beating cycle by a predetermined coefficient (for example, ⅕).

$$\tau_{max}(\theta) = \underset{\tau_{max0} - \frac{T_{QRS}}{2} < \tau < \tau_{max0} + \frac{T_{QRS}}{2}}{\operatorname{argmax}} (u_\theta(\tau))$$ [Mathematical Formula 3]

$$\tau_{min}(\theta) = \underset{\tau_{max0} - \frac{T_{QRS}}{2} < \tau < \tau_{max0} + \frac{T_{QRS}}{2}}{\operatorname{argmin}} (u_\theta(\tau))$$ [Mathematical Formula 4]

In the example, the first relationship is determined based on reference signals (reference fetal electrocardiogram signals) of the fetal electrocardiogram signal expressed by Mathematical Formulas 5 to 7. $ECG_{x0}(\tau)$ denotes a reference fetal electrocardiogram signal of the case where the fetus CB is seen in the negative direction of the x axis. $ECG_{y0}(\tau)$ denotes a reference fetal electrocardiogram signal of the case where the fetus CB is seen in the negative direction of the y axis. $ECG_{z0}(\tau)$ denotes a reference fetal electrocardiogram signal of the case where the fetus CB is seen in the negative direction of the z axis.

$$ECG_{x0}(\tau) = \sum_{i} \alpha_i^x \exp\left[-\frac{(\tau - \tau_i^x)^2}{2(b_i^x)^2}\right] \quad \text{[Mathematical Formula 5]}$$

$$ECG_{y0}(\tau) = \sum_{i} \alpha_i^y \exp\left[-\frac{(\tau - \tau_i^y)^2}{2(b_i^y)^2}\right] \quad \text{[Mathematical Formula 6]}$$

$$ECG_{z0}(\tau) = \sum_{i} \alpha_i^z \exp\left[-\frac{(\tau - \tau_i^z)^2}{2(b_i^z)^2}\right] \quad \text{[Mathematical Formula 7]}$$

In the example, as illustrated in Mathematical Formulas 5 to 7, the reference fetal electrocardiogram signal is expressed by a sum of Gauss functions. Herein, $\alpha_i^x$, $\tau_i^x$, $b_i^x$, $\alpha_i^y$, $\tau_i^y$, $b_i^y$, $\alpha_i^z$, $\tau_i^z$, and $b_i^z$ are parameters specifying Gauss functions. In the example, as illustrated in FIGS. 6 to 8, an electrocardiogram signal disclosed in Non-Patent Literature 1 (R. Sameni, G. D. Clifford, C. Jutten, M. B. Shamsollahi, "Multichannel ECG and noise modeling: Application to maternal and fetal ECG signals", EURASIP Journal on Advances in Signal Processing, 2007, Article ID 43407) is used as a reference fetal electrocardiogram signal.

Figures 9A, 9B:
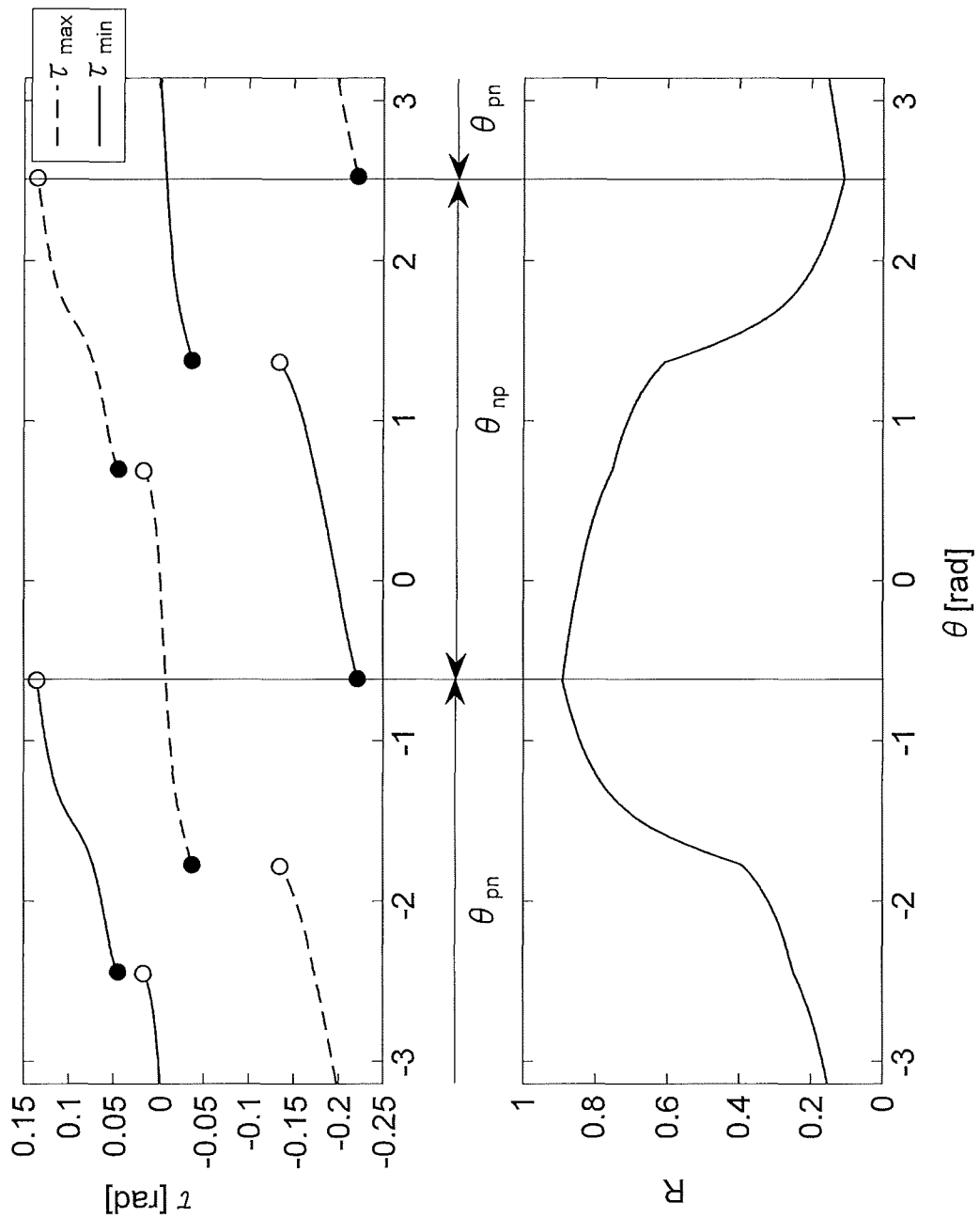
FIGS. 9(A) and 9(B) are graphs illustrating an example of a first relationship stored in the fetal state estimation apparatus illustrated in FIG. 2.

Therefore, the first relationship for the above-described reference fetal electrocardiogram signal is determined so as to be expressed by FIGS. 9(A) and 9(B). In FIG. 9(A), a relationship between the rotation angle θ and the QRS wave time period maximum peak time point $\tau_{max}(\theta)$ is indicated by a broken line, and a relationship between the rotation angle θ and the QRS wave time period minimum peak time point $\tau_{min}(\theta)$ is indicated by a solid line. In FIG. 9(B), a relationship between the rotation angle θ and the signal feature amount $R(\theta)$ is indicated by a solid line.

As illustrated in FIG. 9(A), there exist a range (minimum peak preceding range) $\theta_{np}$ of the rotation angle θ where the QRS wave time period maximum peak time point $\tau_{max}(\theta)$ becomes larger than the QRS wave time period minimum peak time point $\tau_{min}(\theta)$ and a range (maximum peak preceding range) $\theta_{pn}$ of the rotation angle θ where the QRS wave time period maximum peak time point $\tau_{max}(\theta)$ becomes smaller than the QRS wave time period minimum peak time point $\tau_{min}(\theta)$.

As illustrated in FIG. 9(B), in the minimum peak preceding range $\theta_{np}$, the rotation angle θ and the signal feature amount $R(\theta)$ are in one-to-one correspondence to each other. Similarly, in the maximum peak preceding range $\theta_{pn}$ the rotation angle θ and the signal feature amount $R(\theta)$ are in one-to-one correspondence to each other.

The first relationship may be determined based on empirical rules.

The rotation angle estimation unit 211 acquires, for each of the estimated beating time periods, the QRS wave time period maximum peak time point $\tau_{max}(\theta)$ and the QRS wave time period minimum peak time point $\tau_{min}(\theta)$ based on the fetal electrocardiogram base signal $u_\theta(\tau)$.

Furthermore, the rotation angle estimation unit 211 calculates, for each of the estimated beating time periods, the signal feature amount $R(\theta)$ based on the acquired QRS wave time period maximum peak time point $\tau_{max}(\theta)$ the acquired QRS wave time period minimum peak time point $\tau_{min}(\theta)$ and the fetal electrocardiogram base signal $u_\theta(\tau)$.

The rotation angle estimation unit 211 estimates, for each of the estimated beating time periods, the rotation angle θ based on the stored first relationship and the calculated signal feature amount $R(\theta)$.

More specifically, in the case where the acquired QRS wave time period maximum peak time point $\tau_{max}(\theta)$ is larger than the acquired QRS wave time period minimum peak time point $\tau_{min}(\theta)$, the rotation angle estimation unit 211 estimates the rotation angle θ based on a portion corresponding to the minimum peak preceding range $\theta_{np}$ in the stored first relationship and the calculated signal feature amount $R(\theta)$. In the case where the acquired QRS wave time period maximum peak time point $\tau_{max}(\theta)$ is smaller than the acquired QRS wave time period minimum peak time point $\tau_{min}(\theta)$, the rotation angle estimation unit 211 estimates the rotation angle θ based on a portion corresponding to the maximum peak preceding range $\theta_{pn}$ in the stored first relationship and the calculated signal feature amount $R(\theta)$.

By doing so, the rotation angle estimation unit 211 estimates the rotation angle θ at every beating time period.

Figure 10:
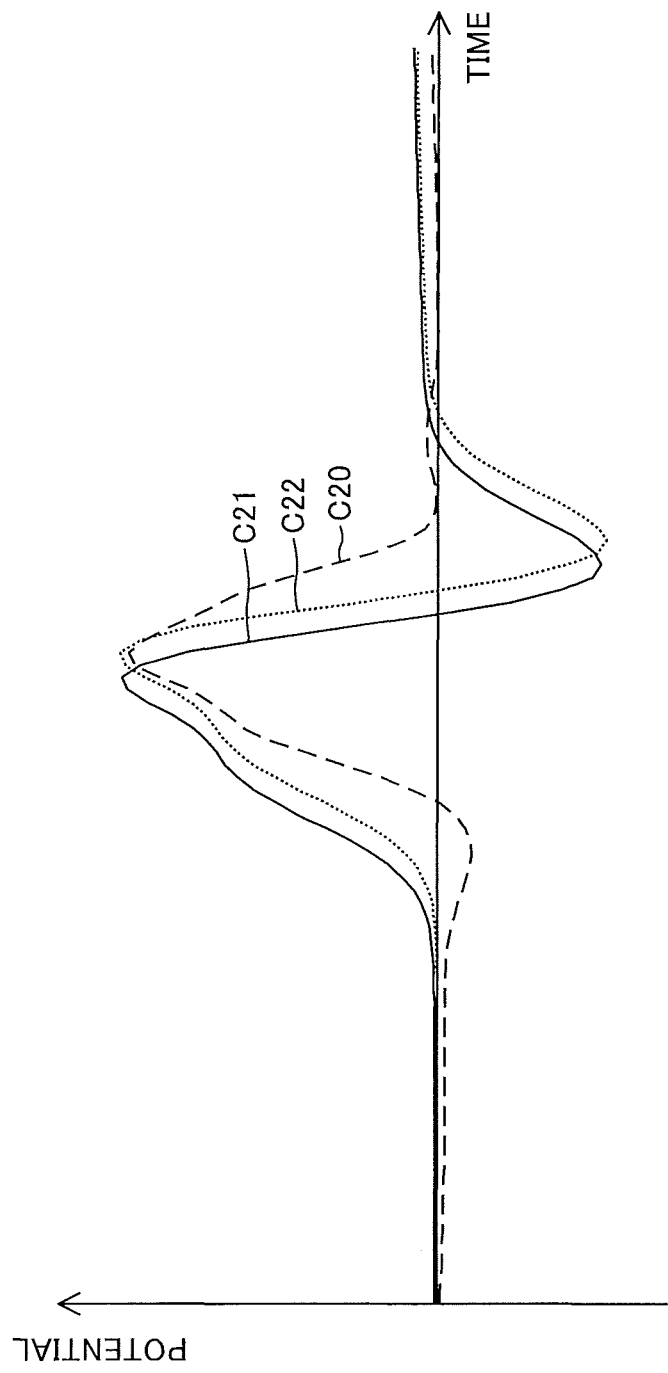
FIG. 10 is a graph illustrating an example of a change in maximum peak time point in the reference fetal electrocardiogram signal according to a rotation angle.

As described above, the maximum peak time point $\tau_{max0}$ in the fetal electrocardiogram base signal is changed according to the rotation angle θ. In FIG. 10, a broken curve C20 represents a reference fetal electrocardiogram signal of the case where the rotation angle is 0 (the case where the fetus CB is seen in the negative direction of the x axis), and a solid curve C21 represents a reference fetal electrocardiogram signal of the case where the rotation angle is different from 0. In this manner, a difference between the time point which is to be the center of the beating time period estimated by the rotation angle estimation unit 211 and the time point which is to be the center of the actual beating time period may be relatively large.

Therefore, the electrocardiogram signal estimation unit 212 re-estimates, for each of the estimated beating time periods, the time point which is to be the center of the beating time period based on the rotation angle θ estimated by the rotation angle estimation unit 211 and re-estimates the beating time period based on the re-estimated time point. In FIG. 10, a dotted curve C22 is a curve obtained by translating the curve C21 by a correction amount of the time point which is to be the center of the beating time period in the time axis.

The re-estimation of the time point which is to be the center of the beating time period will be described.

In the example, the electrocardiogram signal estimation unit 212 stores a relationship (second relationship) between the rotation angle and the rate of change in maximum peak time point in advance.

In the example, the rate of change in maximum peak time point is a parameter calculated based on the QRS wave time period maximum peak time point $\tau_{max}(\theta)$ of the case where the rotation angle is θ and the QRS wave time period maximum peak time point $\tau_{max}(0)$ of the case where the rotation angle is 0. In the example, the rate of change in maximum peak time point $S(\theta)$ is expressed by Mathematical Formula 8.

$$S(\theta) = \frac{\tau_{max}(\theta) - \tau_{max}(0)}{\tau_{max}(\theta) - \tau_{min}(\theta)} \quad \text{[Mathematical Formula 8]}$$

Figure 11:
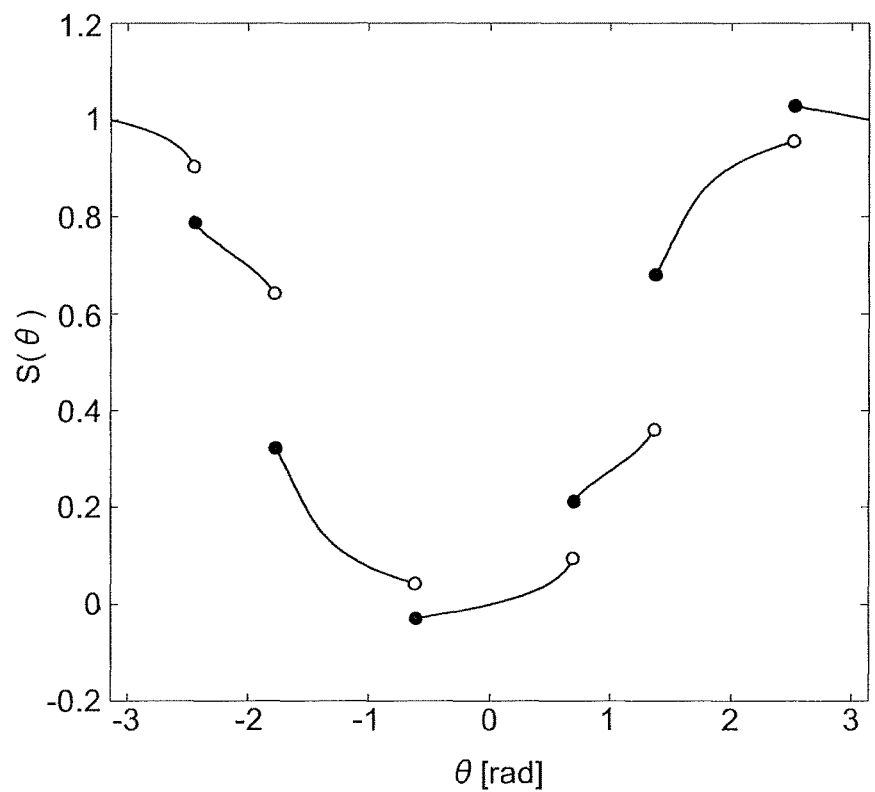
FIG. 11 is a graph illustrating an example of a second relationship stored in the fetal state estimation apparatus illustrated in FIG. 2.

In the example, the second relationship is determined based on the reference fetal electrocardiogram signal expressed by the above-described Mathematical Formulas 5 to 7. Therefore, the second relationship is determined as illustrated in FIG. 11.

The second relationship may be determined based on empirical rules.

The electrocardiogram signal estimation unit 212 acquires, for each of the beating time periods estimated by the rotation angle estimation unit 211, the rate of change in maximum peak time point $S(\theta)$ based on the rotation angle $\theta$ estimated by the rotation angle estimation unit 211 and the stored second relationship.

Next, the electrocardiogram signal estimation unit 212 calculates, for each of the beating time periods estimated by the rotation angle estimation unit 211, the QRS wave time period maximum peak time point $\tau_{max}(0)$ of the case where the rotation angle is 0 based on the acquired rate of change in maximum peak time point $S(\theta)$ and Mathematical Formula 9. The QRS wave time period maximum peak time point $\tau_{max}(0)$ is an example of the maximum value time point.

$$\tau_{max}(0)=\tau_{max}(\theta)-S(\theta)\cdot(\tau_{max}(\theta)-\tau_{min}(\theta)) \quad \text{[Mathematical Formula 9]}$$

The electrocardiogram signal estimation unit 212 estimates, for each of the beating time periods estimated by the rotation angle estimation unit 211, the calculated QRS wave time period maximum peak time point $\tau_{max}(0)$ as a time point which is to be the center of the beating time period.

By doing so, the electrocardiogram signal estimation unit 212 re-estimates the time point which is to be the center of the beating time period.

Then, the electrocardiogram signal estimation unit 212 re-estimates the time period, which starts at a time point which is a time of a half of the beating cycle earlier than the QRS wave time period maximum peak time point $\tau_{max}(0)$ and ends at a time point which is a time of a half of the beating cycle later than the QRS wave time period maximum peak time point $\tau_{max}(0)$, as the beating time period for each of the beating time periods estimated by the rotation angle estimation unit 211.

Next, the electrocardiogram signal estimation unit 212 estimates the electrocardiogram signal (fetal electrocardiogram signal) of the fetus CB with respect to a predetermined reference rotation angle based on the re-estimated beating time period, the rotation angle $\theta$ estimated by the rotation angle estimation unit 211, and the fetal electrocardiogram base signal.

In the example, the electrocardiogram signal estimation unit 212 estimates a first fetal electrocardiogram signal $ECG_x(\tau)$ of the case where the rotation angle is 0 and a second fetal electrocardiogram signal $ECG_y(\tau)$ of the case where the rotation angle is $3\pi/2$. The first fetal electrocardiogram signal $ECG_x(\tau)$ is an example of the electrocardiogram signal of the fetus CB with respect to the first reference rotation angle of 0. The second fetal electrocardiogram signal $ECG_y(\tau)$ is an example of the electrocardiogram signal of the fetus CB with respect to the second reference rotation angle of $3\pi/2$.

In the fetal electrocardiogram base signal, p signal values included in each of the re-estimated beating time periods may be analyzed as a p-dimensional vector. p denotes a natural number and indicates the number of samples. The p signal values included in a plurality of the beating time periods are expressed by one point in a p-dimensional space. Therefore, the fetal electrocardiogram base signal constitutes a set of points, of which the number is equal to the number of beating time periods included in the fetal electrocardiogram base signal, in the p-dimensional space.

The electrocardiogram signal estimation unit 212 acquires first and second main component vectors which are perpendicular to each other by performing a main component analysis on a point set indicating the fetal electrocardiogram base signals in the p-dimensional space.

Next, the electrocardiogram signal estimation unit 212 acquires, for each of the re-estimated beating time periods, the first main component $u_{\theta 1}$ and the second main component $u_{\theta 2}$ of the fetal electrocardiogram base signal in the beating time period. The first main component $u_{\theta 1}$ is a component in the direction along the first main component vector in the fetal electrocardiogram base signal in the beating time period. The second main component $u_{\theta 2}$ is a component in the direction along the second main component vector in the fetal electrocardiogram base signal in the beating time period.

Furthermore, the electrocardiogram signal estimation unit 212 estimates a first rotation angle $\theta_1$ corresponding to the first main component vector and a second rotation angle $\theta_2$ corresponding to the second main component vector. In the example, the electrocardiogram signal estimation unit 212 acquires a QRS wave time period maximum peak time point $\tau_{max}(\theta)$ and a QRS wave time period minimum peak time point $\tau_{min}(\theta)$ for a signal expressed by the first main component vector and calculates a signal feature amount $R(\theta)$ based on the QRS wave time period maximum peak time point $\tau_{max}(\theta)$ and the QRS wave time period minimum peak time point $\tau_{min}(\theta)$. The electrocardiogram signal estimation unit 212 estimates a first rotation angle $\theta_1$ based on the stored first relationship and the calculated signal feature amount $R(\theta)$. Similarly, the electrocardiogram signal estimation unit 212 estimates a second rotation angle $\theta_2$ for a signal expressed by the second main component vector.

The first main component $u_{\theta 1}$ and the second main component $u_{\theta 2}$ are normalized so as to constitute a unit vector. Therefore, the electrocardiogram signal estimation unit 212 performs scaling based on Mathematical Formulas 10 and 11. Herein, $E[X]$ denotes an average of X. $V[X]$ denotes a variance of X. $ECG_{\theta 10}$ denotes a reference fetal electrocardiogram signal of the case where the fetus CB is seen in the direction obtained by rotating the negative direction of the x axis by the first rotation angle $\theta_1$. $ECG_{\theta 20}$ denotes a reference fetal electrocardiogram signal of the case where the fetus CB is seen in the direction obtained by rotating the negative direction of the x axis by the second rotation angle $\theta_2$.

$$ECG_{\theta 1}=u_{\theta 1}\sqrt{V[ECG_{\theta 10}]}+E[ECG_{\theta 10}] \quad \text{[Mathematical Formula 10]}$$

$$ECG_{\theta 2}=u_{\theta 2}\sqrt{V[ECG_{\theta 20}]}+E[ECG_{\theta 20}] \quad \text{[Mathematical Formula 11]}$$

The electrocardiogram signal estimation unit 212 estimates the first and second fetal electrocardiogram signals $ECG_x(\tau)$ and $ECG_y(\tau)$ based on the first and second main components $ECG_{\theta 1}$ and $ECG_{\theta 2}$ after the scaling, the estimated first and second rotation angles $\theta_1$ and $\theta_2$, and Mathematical Formula 12.

$$\begin{bmatrix} ECG_x(\tau) \\ ECG_y(\tau) \end{bmatrix} = \begin{bmatrix} \cos(\theta_1) & -\sin(\theta_1) \\ \cos(\theta_2) & -\sin(\theta_2) \end{bmatrix}^{-1} \cdot \begin{bmatrix} ECG_{\theta 1}(\tau) \\ ECG_{\theta 2}(\tau) \end{bmatrix} \quad \text{[Mathematical Formula 12]}$$

The electrocardiogram signal estimation unit 212 may generate a vector electrocardiogram based on the estimated first fetal electrocardiogram signal $ECG_x(\tau)$ and the estimated second fetal electrocardiogram signal $ECG_y(\tau)$.

The information acquisition unit 220 acquires the living body state information indicating the state of the fetus CB based on the first fetal electrocardiogram signal $ECG_x(\tau)$ estimated by the electrocardiogram signal estimation unit 212. The information acquisition unit 220 may acquire the living body state information based on the second fetal electrocardiogram signal $ECG_y(\tau)$ instead of the first fetal electrocardiogram signal $ECG_x(\tau)$ or in addition to the first fetal electrocardiogram signal $ECG_x(\tau)$.

In the example, the information acquisition unit 220 acquires an RR interval which is a time interval between peaks of consecutive R waves in the first fetal electrocardiogram signal $ECG_x(\tau)$. In other words, the RR interval is a time interval between a peak of an R wave and a peak of another R wave following the former R wave. The R wave is an example of a reference wave, and the RR interval is an example of a reference wave interval.

In the example, for each of a plurality of acquisition time periods which are different from each other, the information acquisition unit 220 acquires the RR intervals included in the acquisition time period. In the example, a length of each of the acquisition time periods is set so that the number of RR intervals included in the acquisition time period is a number within a predetermined range (for example, a range of 300 to 400, or the like). A length of each of acquisition time periods may be a predetermined acquisition time (for example, 1 minute, 5 minutes, 10 minutes, or the like). In this case, the length of the acquisition time period may be constant. The lengths of the acquisition time periods may be different according to the acquisition time periods.

In the example, the plurality of the acquisition time periods is set so that a portion of each of the plurality of the acquisition time periods overlaps a portion of a different acquisition time period. In the example, the plurality of the acquisition time periods is set so that each acquisition time period starts at a time point after a predetermined offset time (in the example, a time corresponding to a heart rate of 100) from a time point when the immediately preceding acquisition time period starts. The heart rate is the number of heartbeats of the fetus CB.

The plurality of the acquisition time periods may be set so that a predetermined non-acquisition time period is disposed between each acquisition time period and an immediately following acquisition time period which immediately follows the acquisition time period. In this case, a length of the non-acquisition time period may be constant. The lengths of the non-acquisition time periods may be different according to the non-acquisition time periods.

Figure 12:
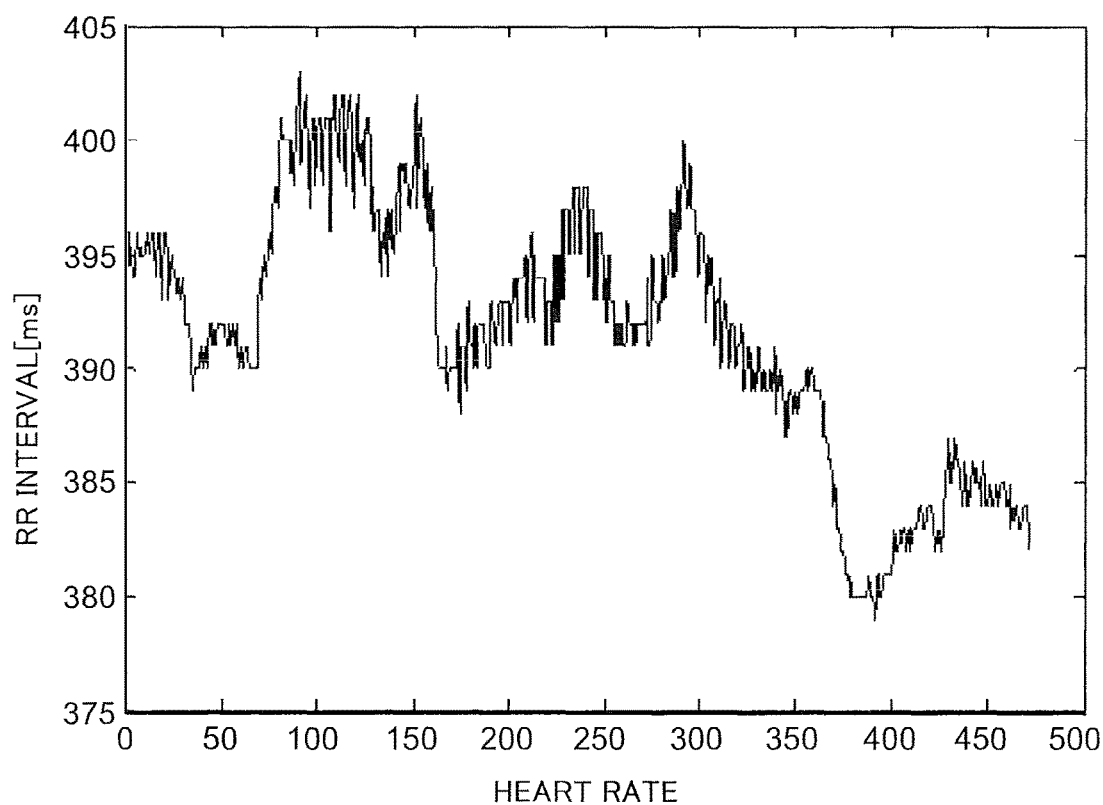
FIG. 12 is a graph illustrating an example of a change in an RR interval to a heart rate.

FIG. 12 is a graph illustrating an example of a change in RR interval to a heart rate.

The information acquisition unit 220 acquires, for each of the plurality of the acquisition time periods, a frequency distribution indicating frequencies of existence of the RR interval included in respective class ranges based on the acquired RR interval.

In the example, the information acquisition unit 220 sets a plurality of class ranges obtained by dividing a distribution range including the acquired RR interval. In the example, a width of the class range is constant. The widths of the class ranges may be different according to the class ranges. The information acquisition unit 220 acquires, for each of the plurality of the acquisition time periods, the frequency distribution by counting the numbers of RR intervals included in the respective class ranges.

The information acquisition unit 220 acquires a normalized frequency distribution based on the acquired frequency distribution for each of the plurality of the acquisition time periods. The normalized frequency distribution is a frequency distribution which is normalized so that a sum of products of the width of the class range and the frequency of the class range becomes 1.

Figure 13:
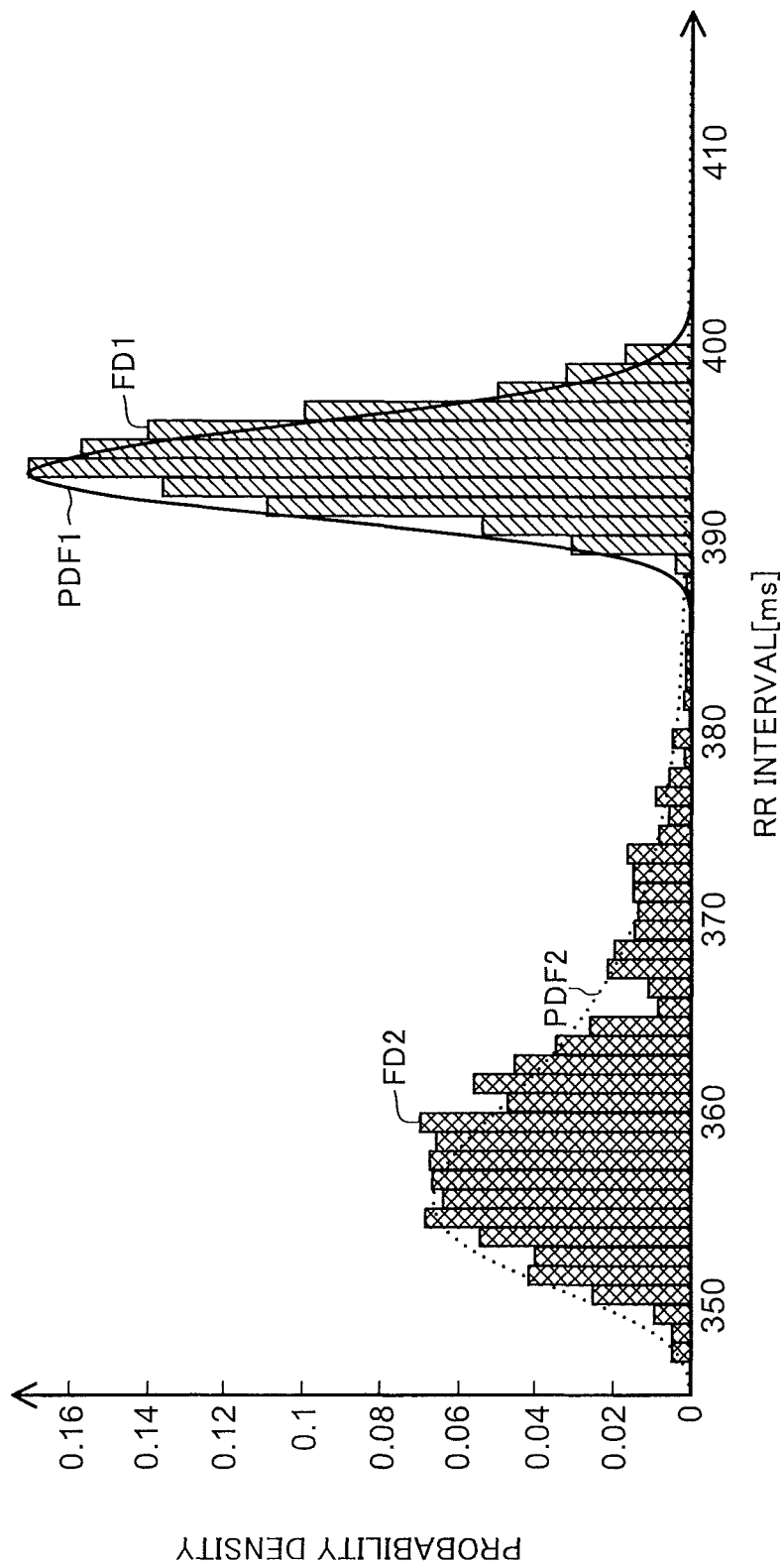
FIG. 13 is a graph illustrating an example of a normalized frequency distribution of an RR interval of a fetus at 23 weeks pregnant.

FIG. 13 is a graph illustrating an example of a normalized frequency distribution of an RR interval of a fetus CB at 23 weeks pregnant. In FIG. 13, rectangles FD1 indicated by slanted hatching represent an example of a normalized frequency distribution of the case where the state of the fetus CB is normal. In FIG. 13, rectangles FD2 indicated by cross hatching represent an example of a normalized frequency distribution of the case where the state of the fetus CB is abnormal.

The information acquisition unit 220 acquires, for each of the plurality of the acquisition time period, a function-specified parameter specifying a predetermined function representing a probability distribution of an RR interval based on the acquired normalized frequency distribution. In the example, the predetermined function representing the probability distribution is a probability density function. In the example, the function is a probability density function $g_\xi(z)$ representing a generalized extreme value distribution expressed by Mathematical Formulas 13 to 15. Herein, z denotes an RR interval as a probability variable.

$$g_\xi(z) = \frac{1}{\sigma}\left(1 + \xi\frac{(z-\mu)}{\sigma}\right)^{-1-\frac{1}{\xi}} \quad \text{[Mathematical Formula 13]}$$

$$\exp\left\{-\left(1 + \xi\frac{(z-\mu)}{\sigma}\right)^{-\frac{1}{\xi}}\right\}$$

$$1 + \xi\frac{(z-\mu)}{\sigma} > 0 \quad \text{[Mathematical Formula 14]}$$

$$g_\xi(z) = \frac{1}{\sigma}\exp\left\{-\frac{(z-\mu)}{\sigma} - \exp\left(-\frac{(z-\mu)}{\sigma}\right)\right\} \quad \text{[Mathematical Formula 15]}$$

$\mu$ denotes a position parameter; $\sigma$ denotes a scale parameter; and $\xi$ denotes a shape parameter. In the example, the position parameter $\mu$, the scale parameter $\sigma$, and the shape parameter $\xi$ are examples of the function-specified parameters.

Mathematical Formula 13 expresses a probability density function $g_\xi(z)$ of the case where the shape parameter $\xi$ is not 0 and the probability variable z satisfies the condition expressed by Mathematical Formula 14. In the case where the shape parameter $\xi$ is not 0 and the probability variable z does not satisfy the condition expressed by Mathematical Formula 14, the probability density function $g_\xi(z)$ is 0.

Mathematical Formula 15 expresses a probability density function $g_\xi(z)$ of the case where the shape parameter $\xi$ is 0.

The probability distribution of an RR interval is well represented by the generalized extreme value distribution. Therefore, the shape parameter $\xi$ of the generalized extreme value distribution represents the state of the fetus CB with high accuracy. For this reason, according to the fetal state estimation apparatus 1 of the first embodiment, it is possible to acquire information indicating the state of the fetus CB with high accuracy.

In the example, the shape parameter $\xi$ is an example of the living body state information. The living body state information may be any one of or a combination of the position parameter μ, the scale parameter σ, and the shape parameter ξ.

For example, the information acquisition unit 220 estimates the function-specified parameter using a maximum likelihood method. The information acquisition unit 220 may estimate the function-specified parameter using a method such as a least square method different from the maximum likelihood method.

In FIG. 13, a sold curve PDF1 represents a probability density function $g_\xi(z)$ specified by the function-specified parameter acquired for the normalized frequency distribution FD1 of the case where the state of the fetus CB is normal. In FIG. 13, a dotted curve PDF2 represents a probability density function $g_\xi(z)$ specified by the function-specified parameter acquired for the normalized frequency distribution FD2 of the case where the state of the fetus CB is abnormal.

Figure 14:
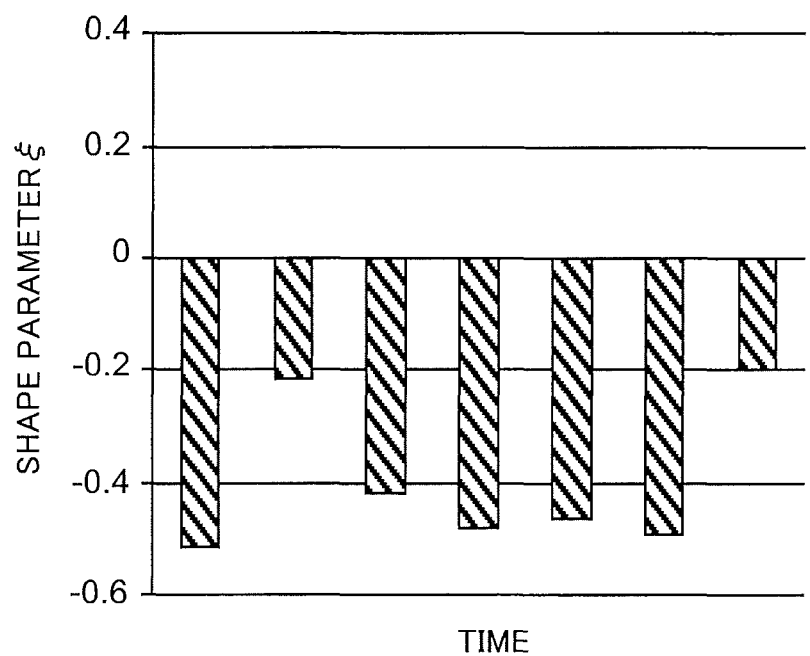
FIG. 14 is a graph illustrating an example of a change in a shape parameter in the case where the state of the fetus at 23 weeks pregnant is normal.

FIG. 14 is a graph illustrating an example of a change in a shape parameter for each of the plurality of the acquisition time periods in the case where the state of the fetus CB at 23 weeks pregnant is normal.

Figure 15:
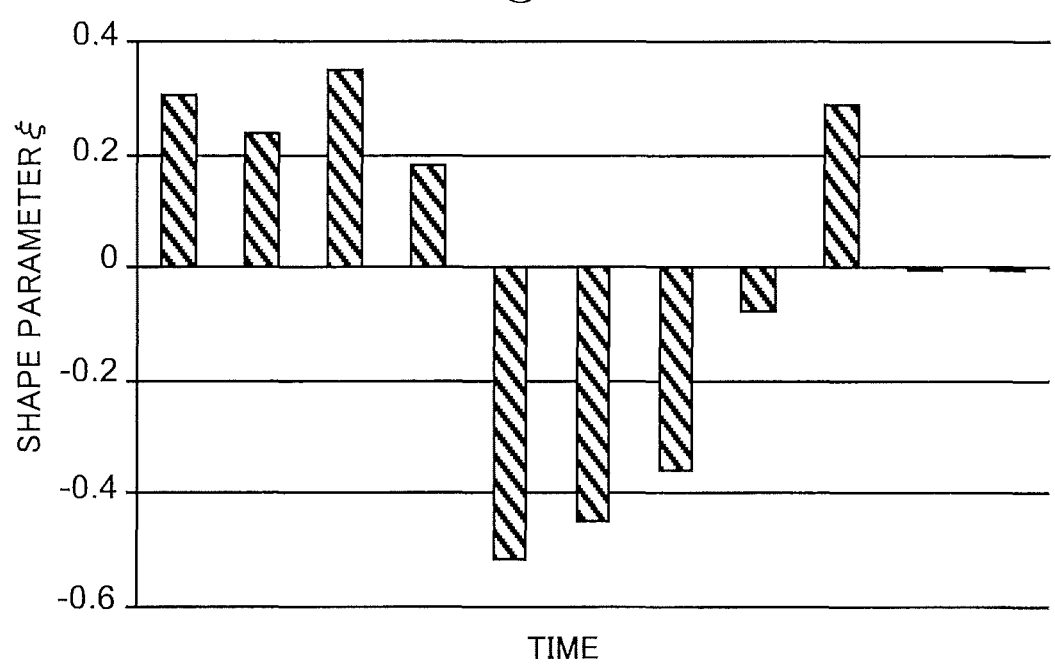
FIG. 15 is a graph illustrating an example of a change in a shape parameter in the case where the state of the fetus at 23 weeks pregnant is abnormal.

FIG. 15 is a graph illustrating an example of a change in a shape parameter ξ for each of the plurality of the acquisition time periods in the case where the state of the fetus CB at 23 weeks pregnant is abnormal.

In this manner, the case where the state of the fetus CB is abnormal has a higher probability that the shape parameter ξ has a positive value than the case where the state of the fetus CB is normal.

Therefore, in the case where the shape parameter ξ acquired by the information acquisition unit 220 has a positive value, the living body state determination unit 230 determines that the state of the fetus CB is abnormal. On the other hand, in the case where the shape parameter ξ acquired by the information acquisition unit 220 has a negative value, the living body state determination unit 230 determines that the state of the fetus CB is normal.

In the case where the shape parameter ξ is equal to or larger than a predetermined positive determination threshold value (for example, 0.1), the living body state determination unit 230 may determine that the state of the fetus CB is abnormal; and in the case where the shape parameter ξ is smaller than the determination threshold value, the living body state determination unit 230 may determine that the state of the fetus CB is normal.

In the case where a frequency of the shape parameters ξ having a positive value, the number of consecutive acquisition time periods when the shape parameter ξ has a positive value, an average value of the shape parameters ξ, or a variance of the shape parameters ξ is equal to or larger than a predetermined determination threshold value, the living body state determination unit 230 may determine that the state of the fetus CB is abnormal.

The living body state determination unit 230 may determine based on information entropy for time-series data of the shape parameter ξ whether the state of the fetus CB is normal.

For example, the living body state determination unit 230 may use the shape parameters $\xi_0, \xi_1, \ldots, \xi_m$ for respective m acquisition time periods as the m pieces of time-series data $\xi_0, \xi_1, \ldots, \xi_m$ of the shape parameter ξ and may calculate information entropy H for the m pieces of time-series data of the shape parameter ξ based on Mathematical Formula 16. m denotes integer more than 1.

$$H = -\int p(\xi_0, \xi_1, \ldots, \xi_m) \log p(\xi_0, \xi_1, \ldots, \xi_m) dv$$

[Mathematical Formula 16]

Herein, $p(\xi_0, \xi_1, \ldots, \xi_m)$ denotes joint probability distribution of time-series data $\xi_0, \xi_1, \ldots, \xi_m$.

In this case, the living body state determination unit 230 calculates the information entropy at every acquisition of a new shape parameter ξ. Furthermore, the living body state determination unit 230 determines that the state of the fetus CB is abnormal in the case where the calculated information entropy becomes larger than a value obtained by a previously calculated value plus a predetermined increase threshold value (for example, 0).

The living body state determination unit 230 may determine whether the state of the maternal body MB is normal in addition to the state of the fetus CB or instead of the state of the fetus CB.

The output unit 30 outputs information indicating the result of determination performed by the living body state determination unit 230. The output unit 30 may output (for example, display on a display) information (for example, a graph) indicating a change in the living body state information to time acquired by the information acquisition unit 220. The output unit 30 may store the information in a storage device in addition to outputting the information or instead of outputting the information.

(Operations)

Next, operations of the above-described fetal state estimation apparatus 1 will be described with reference to FIG. 16.

First, the electrodes 11 to 15 are attached to a surface (for example, skin) MBS of the abdomen of a pregnant maternal body MB.

Figure 16:
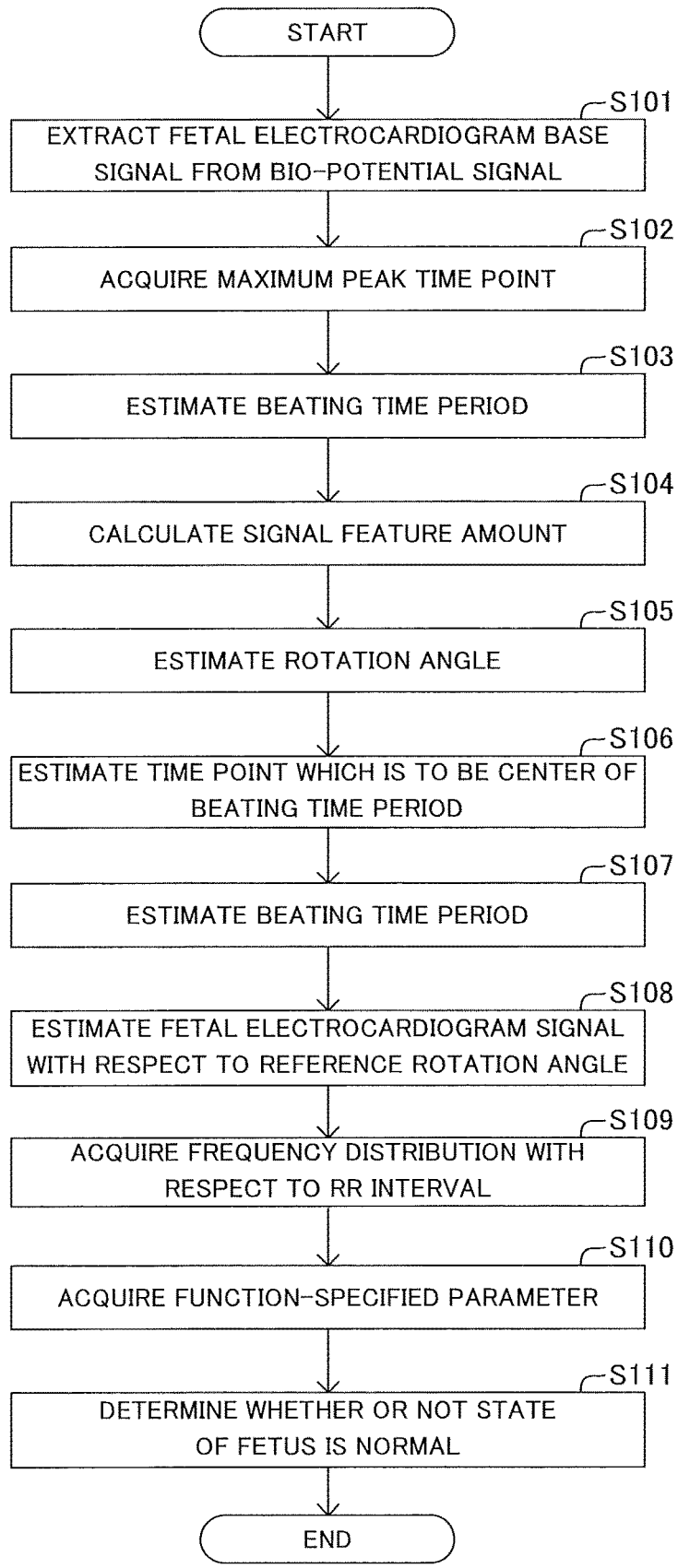
FIG. 16 is a flowchart illustrating an example of a process performed by the fetal state estimation apparatus illustrated in FIG. 2.

The fetal state estimation apparatus 1 extracts the fetal electrocardiogram base signal from the bio-potential signal measured by the measurement unit 10 using the ICA (Step S101 of FIG. 16).

Next, the fetal state estimation apparatus 1 estimates boundary time points and acquires the maximum peak time point $\tau_{max0}$ when the fetal electrocardiogram base signal $u_\theta(\tau)$ has a maximum value in a time period between consecutive two boundary time points among the estimated boundary time points (Step S102 of FIG. 16).

Then, the fetal state estimation apparatus 1 estimates the time period, which starts at a time point which is a time of a half of the beating cycle earlier than the maximum peak time point $\tau_{max0}$ and ends at a time point which is a time of a half of the beating cycle later than the maximum peak time point $\tau_{max0}$, as the beating time period (Step S103 of FIG. 16).

Next, the fetal state estimation apparatus 1 acquires the QRS wave time period maximum peak time point $\tau_{max}(\theta)$ and the QRS wave time period minimum peak time point $\tau_{min}(\theta)$ for each of the estimated beating time periods. Then, the fetal state estimation apparatus 1 calculates, for each of the estimated beating time periods, the signal feature amount $R(\theta)$ based on the acquired QRS wave time period maximum peak time point $\tau_{max}(\theta)$, the acquired QRS wave time period minimum peak time point $\tau_{min}(s)$, and the fetal electrocardiogram base signal $u_\theta(\tau)$ (Step S104 of FIG. 16).

Next, the fetal state estimation apparatus 1 estimates, for each of the estimated beating time periods, the rotation angle θ based on the stored first relationship and the calculated signal feature amount $R(\theta)$ (Step S105 of FIG. 16).

Then, the fetal state estimation apparatus 1 acquires, for each of the estimated beating time periods, the rate of change in maximum peak time point $S(\theta)$ based on the estimated rotation angle θ and the stored second relationship. Furthermore, the fetal state estimation apparatus 1 calculates, for each of the estimated beating time periods, the QRS wave time period maximum peak time point $\tau_{max}$ (0) of the case where the rotation angle is 0 based on the acquired rate of change in maximum peak time point $S(\theta)$. Next, the fetal state estimation apparatus 1 estimates the calculated QRS wave time period maximum peak time point $\tau_{max}$ (0) as the time point which is to be the center of the beating time period (Step S106 of FIG. 16).

Then, the fetal state estimation apparatus 1 re-estimates, for each of the estimated beating time periods, the time period, which starts at a time point which is a time of a half of the beating cycle earlier than the QRS wave time period maximum peak time point $\tau_{max}$ (0) and ends at a time point which is a time of a half of the beating cycle later than the QRS wave time period maximum peak time point $\tau_{max}$ (0), as the beating time period (Step S107 of FIG. 16).

Next, the fetal state estimation apparatus 1 estimates the fetal electrocardiogram signal with respect to the reference rotation angle based on the re-estimated beating time period, the estimated rotation angle θ, and the extracted fetal electrocardiogram base signal (Step S108 of FIG. 16). In the example, the fetal state estimation apparatus 1 estimates the first fetal electrocardiogram signal with respect to the first reference rotation angle and the second fetal electrocardiogram signal with respect to the second reference rotation angle.

Then, the fetal state estimation apparatus 1 acquires RR intervals for each of the plurality of the acquisition time periods based on the estimated first fetal electrocardiogram signal. Next, the fetal state estimation apparatus 1 acquires, for each of the plurality of the acquisition time periods, the frequency distribution of the RR intervals based on the acquired RR intervals. The fetal state estimation apparatus 1 acquires, for each of the plurality of the acquisition time periods, the normalized frequency distribution based on the acquired frequency distribution (Step S109 of FIG. 16)

Next, the fetal state estimation apparatus 1 acquires, for each of the plurality of the acquisition time periods, a function-specified parameter based on the acquired normalized frequency distribution (Step S110 of FIG. 16).

Then, the fetal state estimation apparatus 1 determines based on the acquired function-specified parameter whether the state of the fetus CB is normal (Step S111 of FIG. 16).

As described hereinbefore, the fetal state estimation apparatus 1 according to the first embodiment acquires a parameter specifying the probability density function representing the probability density of RR intervals in the acquired electrocardiogram signal as the information indicating the state of the fetus CB.

Accordingly, it is possible to acquire information indicating the state of the fetus CB with high accuracy.

Furthermore, the fetal state estimation apparatus 1 according to the first embodiment estimates the rotation angle of the fetus CB with respect to the maternal body MB at every beating of the heart of the fetus CB based on the bio-potential signal indicating a change in potential on the surface MBS of the maternal body MB. The fetal state estimation apparatus 1 estimates an electrocardiogram signal with respect to a predetermined reference rotation angle based on the bio-potential signal and the estimated rotation angle.

The appearing shape of a change in electromotive force of heart of the fetus CB in the electrocardiogram signal is changed according to the rotation angle of the fetus CB with respect to the maternal body MB. Therefore, according to the fetal state estimation apparatus 1 of the first embodiment, it is possible to acquire an electrocardiogram signal where a change in the appearing shape of the change in electromotive force of heart of the fetus CB in the electrocardiogram signal is suppressed. As a result, it is possible to acquire information indicating the state of the fetus CB with high accuracy.

The fetal state estimation apparatus 1 according to the first embodiment estimates the electrocardiogram base signal caused by the beating of the heart of the fetus CB. Furthermore, the fetal state estimation apparatus 1 calculates the predetermined signal feature amount based on the maximum and minimum values of the estimated electrocardiogram base signal in a predetermined target time period at every beating of the heart of the fetus CB. The fetal state estimation apparatus 1 estimates the rotation angle based on the calculated signal feature amount at every beating of the heart of the fetus CB.

The rotation angle of the fetus CB with respect to the maternal body MB at every beating of the heat of the fetus CB is represented well by the relationship between the maximum and minimum values of the electrocardiogram base signal in the predetermined target time period. Therefore, according to the fetal state estimation apparatus 1 of the first embodiment, it is possible to estimate the rotation angle of the fetus CB with respect to the maternal body MB with high accuracy.

Furthermore, the fetal state estimation apparatus 1 according to the first embodiment estimates the maximum value time point which is a time point when the electrocardiogram signal with respect to a predetermined reference rotation angle has a maximum value based on a time point when the estimated electrocardiogram base signal has a maximum value in the target time period and the estimated rotation angle at every beating of the heart of the fetus CB. The fetal state estimation apparatus 1 estimates the electrocardiogram signal based on the estimated maximum value time point, the estimated rotation angle, and the estimated electrocardiogram base signal.

The appearing shape of the change in electromotive force of heart of the fetus CB in the electrocardiogram base signal is changed according to the rotation angle of the fetus CB with respect to the maternal body MB. Therefore, according to the fetal state estimation apparatus 1 of the first embodiment, it is possible to estimate the maximum value time point when the electrocardiogram signal has a maximum value with high accuracy at every beating of the heart of the fetus CB. As a result, it is possible to estimate the electrocardiogram signal with high accuracy based on the estimated maximum value time point. Accordingly, it is possible to acquire information indicating the state of the fetus CB with high accuracy.

The fetal state estimation apparatus 1 according to the first embodiment estimates the electrocardiogram base signal using an Independent Component Analysis.

Accordingly, it is possible to estimate the electrocardiogram base signal with high accuracy.

The fetal state estimation apparatus 1 may be used for a fetus CB at earlier than 23 weeks pregnant or a fetus CB at later than 23 weeks pregnant.

Although the fetal state estimation apparatus 1 acquires the living body state information based on an electrocardiogram signal with respect to a predetermined reference rotation angle, the fetal state estimation apparatus 1 may acquire the living body state information based on an electrocardiogram base signal.

The fetal state estimation apparatus 1 is used for a fetus CB. However, the living body state estimation apparatus according to the present invention may be used for a human being after birth (a newborn baby, a baby, an infant, a child, an adult, or the like). In this case, preferably, the living body state estimation apparatus acquires an electrocardiogram signal using a well-known method such as a 12-lead electrocardiogram method and acquires living body state information based on the acquired electrocardiogram signal.

Although the fetal state estimation apparatus 1 uses the probability density function representing the generalized extreme value distribution as a predetermined function representing the probability distribution, the fetal state estimation apparatus 1 may use a probability density function representing a different probability distribution such as a negative hypergeometric distribution (beta binominal distribution). For example, a modified example where the fetal state estimation apparatus 1 uses a probability density function representing a beta binominal distribution as a predetermined function representing a probability distribution will be described. In this case, the predetermined function representing the probability distribution is expressed by Mathematical Formulas 17 and 18 and is a probability density function $g_\beta(z)$ representing the beta binominal distribution. Herein, z denotes an RR interval as a probability variable.

$$g_\beta(z) = \frac{1}{\beta(a, b)} z^{a-1}(1-z)^{b-1}$$ [Mathematical Formula 17]

$$0 \leq z \leq 1$$ [Mathematical Formula 18]

$\beta(a, b)$ denotes a beta function; a denotes a first parameter; and b denotes a second parameter. In the example, the first parameter a and the second parameter b are examples of a function-specified parameter.

Mathematical Formula 17 expresses a probability density function $g_\beta(z)$ of the case where the probability variable z satisfies the condition expressed by Mathematical Formula 18. In the case where the probability variable z does not satisfy the condition expressed by Mathematical Formula 18, the probability density function $g_\beta(z)$ is 0.

A probability distribution of an RR interval is well represented by the beta binominal distribution. Therefore, the first parameter a and the second parameter b of the beta binominal distribution represent the state of the fetus CB with high accuracy. For this reason, according to the fetal state estimation apparatus 1 of the modified example, it is possible to acquire information indicating the state of the fetus CB with high accuracy.

In the example, the first parameter a and the second parameter b are examples of the living body state information. In the example, in the case where a value a/b obtained by dividing the first parameter a by the second parameter b is smaller than 1, the fetal state estimation apparatus 1 determines that the state of the fetus CB is abnormal. On the other hand, in the case where the value a/b obtained by dividing the first parameter a by the second parameter b is equal to or larger than 1, the fetal state estimation apparatus 1 determines that the state of the fetus CB is normal.

The living body state information may be any one of the first parameter a and the second parameter b.

For example, the fetal state estimation apparatus 1 may use the generalized extreme value distribution for a fetus CB from 20 to 27 weeks pregnant and may use the beta binominal distribution for a fetus CB on or after 28 weeks pregnant. Autonomic nervous system of a fetus CB develops on or after 28 weeks pregnant. Therefore, the fetal state estimation apparatus 1 preferably uses the beta binominal distribution for a fetus CB on or after 28 weeks pregnant.

The fetal state estimation apparatus 1 may not include the living body state determination unit 230 as a function. In this case, preferably, the fetal state estimation apparatus 1 outputs (for example, displays on a display) information (for example, a graph) indicating a change in the living body state information to time acquired by the information acquisition unit 220.

Hereinbefore, while the present invention has been described with reference to the above-described embodiments, the present invention is not limited to the above-described embodiments. It may be understood by the skilled in the related art that various changes may be available to configurations and details of the present invention within the scope of the present invention.

Any combination of the above-described embodiments and modified examples may be employed as other modified examples of the above-described embodiments within the scope without departing from the spirit of the present invention.

What is claimed is:

1. A living body state estimation apparatus comprising processor circuitry,
the processor circuitry configured to:
acquire an electrocardiogram signal of the living body within an electrocardiogram signal acquisition unit;
acquire a parameter as the information indicating the state of the living body using the acquired electrocardiogram signal as an input, and
estimate the living body state from the acquired parameter, wherein
to acquire the parameter comprises:
setting at least one predetermined acquisition time period including a plurality of reference wave intervals each of which is a time interval between peaks of consecutive predetermined reference waves in the acquired electrocardiogram signal,
dividing a distribution range including the plurality of reference wave intervals acquired from the acquisition time interval by a constant time interval to obtain a plurality of class ranges,
acquiring, for each class range obtained by the dividing, a normalized frequency distribution indicating a frequency of existence of the plurality of reference wave intervals included in the class range, and
acquiring the parameter specifying a predetermined function indicating a probability distribution for the plurality of reference wave intervals based on the normalized frequency distribution.

2. The living body estimation apparatus according to claim 1,
wherein the function is a function representing a generalized extreme value distribution, and
wherein the parameter is a shape parameter of the generalized extreme value distribution.

3. The living body state estimation apparatus according to claim 2, further the processor circuitry configured to determine that the state of the living body is abnormal in the case where the acquired shape parameter has a positive value.

4. The living body state estimation apparatus according to claim 1,
wherein the living body is a fetus in a maternal body, and
wherein the processor circuitry is configured to:
estimate a rotation angle of the fetus with respect to the maternal body at every beating of the heart of the fetus based on a potential signal indicating a change in potential on a surface of the maternal body; and estimate the electrocardiogram signal with respect to a predetermined reference rotation angle based on the potential signal and the estimated rotation angle.

5. The living body state estimation apparatus according to claim 4, wherein the estimating of the rotation angle comprises estimating an electrocardiogram base signal caused by the beating of the heart of the fetus, calculating a predetermined signal feature amount based on maximum and minimum values of the estimated electrocardiogram base signal in a predetermined target time period at every beating of the heart of the fetus, and estimating the rotation angle based on the calculated signal feature amount at every beating of the heart of the fetus.

6. The living body state estimation apparatus according to claim 5, wherein the signal feature amount is a value obtained by dividing the maximum value by a value obtained by subtracting the minimum value from the maximum value.

7. The living body state estimation apparatus according to claim 5, wherein the estimating of the electrocardiogram signal comprises estimating, at every beating of the heart of the fetus, a maximum value time point which is a time point when the electrocardiogram signal with respect to a predetermined reference rotation angle has a maximum value based on a time point when the estimated electrocardiogram base signal has a maximum value in the target time period and the estimated rotation angle and estimating the electrocardiogram signal based on the estimated maximum value time point, the estimated rotation angle, and the estimated electrocardiogram base signal.

8. The living body state estimation apparatus according to claim 5, wherein the estimating of the rotation angle comprises estimating the electrocardiogram base signal by using an independent component analysis.

9. A living body state estimating method for acquiring information indicating a state of a living body, the living body state estimating method comprising:

acquiring, within an electrocardiogram signal acquisition unit, an electrocardiogram signal of the living body;

acquiring a parameter as the information indicating the state of the living body using the acquired electrocardiogram signal as an input, and estimating the living body state from the acquired parameter, wherein the acquiring of the parameter comprising:

setting at least one predetermined acquisition time period including a plurality of reference wave intervals each of which is a time interval between peaks of consecutive predetermined reference waves in the acquired electrocardiogram signal;

dividing a distribution range including the plurality of reference wave intervals acquired from the acquisition time interval by a constant time interval to obtain a plurality of class ranges;

acquiring, for each class range obtained by the dividing, a normalized frequency distribution indicating a frequency of existence of the plurality of reference wave intervals included in the class range; and acquiring the parameter specifying a predetermined function indicating a probability distribution for the plurality of reference wave intervals based on the normalized frequency distribution.

10. The living body state estimating method according to claim 9, wherein the function is a function representing a generalized extreme value distribution, and wherein the parameter is a shape parameter of the generalized extreme value distribution.

11. The living body state estimating method according to claim 9, wherein the living body is a fetus in a maternal body, and wherein the acquiring of the electrocardiogram signal comprises:

estimating a rotation angle of the fetus with respect to the maternal body at every beating of the heart of the fetus based on a potential signal indicating a change in potential on a surface of the maternal body; and estimating the electrocardiogram signal with respect to a predetermined reference rotation angle based on the potential signal and the estimated rotation angle.

12. The living body state estimating method according to claim 11, wherein the estimating of the rotation angle comprises:

estimating an electrocardiogram base signal caused by the beating of the heart of the fetus;

calculating a predetermined signal feature amount based on maximum and minimum values of the estimated electrocardiogram base signal in a predetermined target time period at every beating of the heart of the fetus; and estimating the rotation angle based on the calculated signal feature amount at every beating of the heart of the fetus.

13. The living body state estimating method according to claim 11, wherein the estimating of the electrocardiogram signal comprises:

estimating a maximum value time point which is a time point when the electrocardiogram signal with respect to a predetermined reference rotation angle has a maximum value based on a time point when the estimated electrocardiogram base signal has a maximum value in the target time period and the estimated rotation angle at every beating of the heart of the fetus; and estimating the electrocardiogram signal based on the estimated maximum value time point, the estimated rotation angle, and the estimated electrocardiogram base signal.

14. A non-transitory computer-readable medium that stores a living body state estimating program for causing a computer to execute a process of acquiring information indicating a state of a living body, the process comprising:

acquiring, within an electrocardiogram signal acquisition unit, an electrocardiogram signal of the living body;

acquiring a parameter as the information indicating the state of the living body using the acquired electrocardiogram signal as an input, and estimating the living body state from the acquired parameter, wherein the acquiring of the parameter comprising:

setting at least one predetermined acquisition time period including a plurality of reference wave intervals each of which is a time interval between peaks of consecutive predetermined reference waves in the acquired electrocardiogram signal;

dividing a distribution range including the plurality of reference wave intervals acquired from the acquisition time interval by a constant time interval to obtain a plurality of class ranges;

acquiring, for each class range obtained by the dividing, a normalized frequency distribution indicating a frequency of existence of the plurality of reference wave intervals included in the class range; and acquiring the parameter specifying a predetermined function indicating a probability distribution for the plurality of reference wave intervals based on the normalized frequency distribution.

15. The non-transitory computer-readable medium according to claim 14,
wherein the function is a function representing a generalized extreme value distribution, and
wherein the parameter is a shape parameter of the generalized extreme value distribution.

16. The non-transitory computer-readable medium according to claim 14,
wherein the living body is a fetus in a maternal body, and
wherein the acquiring of the electrocardiogram signal comprises:
estimating a rotation angle of the fetus with respect to the maternal body at every beating of the heart of the fetus based on a potential signal indicating a change in potential on a surface of the maternal body; and
estimating the electrocardiogram signal with respect to a predetermined reference rotation angle based on the potential signal and the estimated rotation angle.

17. The non-transitory computer-readable medium according to claim 16, wherein the estimating of the rotation angle comprises:
estimating an electrocardiogram base signal caused by the beating of the heart of the fetus;
calculating a predetermined signal feature amount based on maximum and minimum values of the estimated electrocardiogram base signal in a predetermined target time period at every beating of the heart of the fetus; and
estimating the rotation angle based on the calculated signal feature amount at every beating of the heart of the fetus.

18. The non-transitory computer-readable medium according to claim 16, wherein the estimating of the electrocardiogram signal comprises:
estimating a maximum value time point which is a time point when the electrocardiogram signal with respect to a predetermined reference rotation angle has a maximum value based on a time point when the estimated electrocardiogram base signal has a maximum value in the target time period and the estimated rotation angle at every beating of the heart of the fetus; and
estimating the electrocardiogram signal based on the estimated maximum value time point, the estimated rotation angle, and the estimated electrocardiogram base signal.

* * * * *